(12) United States Patent
Turkevych

(10) Patent No.: US 9,733,162 B2
(45) Date of Patent: Aug. 15, 2017

(54) UNIVERSAL SYSTEM, METHOD AND SOLUTION FOR THE ACCELERATION OF THE PROCESS OF FIXING, DEHYDRATING AND CLEARING THE STRUCTURE OF BIOLOGICAL TISSUE

(71) Applicant: Ihor Turkevych, Southampton, PA (US)

(72) Inventor: Ihor Turkevych, Southampton, PA (US)

( * ) Notice: Subject to any disclaimer, the term of this patent is extended or adjusted under 35 U.S.C. 154(b) by 24 days.

(21) Appl. No.: 14/557,758

(22) Filed: Dec. 2, 2014

(65) Prior Publication Data

US 2015/0226650 A1 Aug. 13, 2015

Related U.S. Application Data

(60) Provisional application No. 61/938,189, filed on Feb. 11, 2014.

(51) Int. Cl.
*G01N 1/30* (2006.01)

(52) U.S. Cl.
CPC ......... *G01N 1/30* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 4,066,582 A * | 1/1978 | Babian | C09D 4/00 522/153 |
| 4,698,312 A | 10/1987 | Wong | |
| 5,422,277 A | 6/1995 | Connelly | |
| 5,862,806 A * | 1/1999 | Cheung | A61L 27/3604 128/898 |
| 5,882,850 A * | 3/1999 | Khor | A61L 27/3604 435/1.1 |
| 6,291,180 B1 | 9/2001 | Chu | |
| 7,666,620 B2 | 2/2010 | Wiederhold | |
| 7,887,811 B2 | 2/2011 | Zagury | |
| 2001/0016317 A1 | 8/2001 | Berger | |
| 2002/0009722 A1 | 1/2002 | Berger | |
| 2005/0084924 A1 | 4/2005 | Shults | |
| 2005/0090017 A1 | 4/2005 | Morales | |
| 2007/0037138 A1 | 2/2007 | Winther | |
| 2007/0110666 A1 | 5/2007 | Pevsner | |
| 2009/0155838 A1 | 6/2009 | Hale | |
| 2009/0226059 A1 | 9/2009 | Levenson | |
| 2010/0068690 A1 | 3/2010 | Liotta | |
| 2010/0255524 A1 | 10/2010 | Hollander | |
| 2012/0149019 A1 | 6/2012 | Josel | |
| 2013/0137094 A1 | 5/2013 | Espina | |

FOREIGN PATENT DOCUMENTS

| | | |
|---|---|---|
| WO | WO9407532 | 4/1994 |
| WO | WO9958166 | 11/1999 |
| WO | WO 2015/123192 | 8/2015 |

OTHER PUBLICATIONS

Khor et al, Dimethyl sulfoxide as an anticalcification agent for glutaraldehyde-fixed biological tissue, Journal of Materials Science-Materials in Medicine7.11 (Nov. 1996): 691-693.
Manston et al., Demonstration of mitochondrial mineral deposits in osteoblasts after anhydrous fixation and processing, Journal of microscopy134.Pt 2 (May 1984): 177-82.
Inch et al, Histological and anatomical responses in avocado,*Persea americana*, induced by the vascular wiltpathogen, Raffaelea lauricola, Botany, 90.7 (Jul. 2012): 627(9).
Wang et al, Ultrasound Facilitated Formalin-fixed and Paraffin-embedded Tissue Specimen Preparation Technology, 2008 BRN Symposium Poster available at biospecimens.cancer.gov/meeting/brnsymposium/docs/2008pres/Poster27-Wang.pdf.
Chu et al, Ultrasound-accelerated formalin fixation of tissue improves morphology, antigen and mRNA preservation, Modern Pathology (2005) 18, 850-863, advance online publication, Dec. 17, 2004.

\* cited by examiner

*Primary Examiner* — Robert Yamasaki
(74) *Attorney, Agent, or Firm* — Howson & Howson LLP

(57) ABSTRACT

Described herein are methods, compositions, kits and systems for fixing biological samples. In one aspect, the method includes contacting the tissue sample with a fixing composition comprising about 20 to about 80% v/v DMSO. The solutions of the dehydration and clearing steps also include DMSO. Tissues fixed according to the methods described herein (and using the compositions herein described) may be fixed at a more rapid rate as compared to conventional procedures, but with comparable results.

6 Claims, 37 Drawing Sheets

UNIVERSAL SYSTEM, METHOD AND SOLUTION FOR THE ACCELERATION OF THE PROCESS OF FIXING, DEHYDRATING AND CLEARING THE STRUCTURE OF BIOLOGICAL TISSUE

CROSS REFERENCE TO RELATED APPLICATIONS

This application claims priority to U.S. Provisional Patent Application No. 61/938,189, filed Feb. 11, 2014. This application is incorporated herein by reference in its entirety.

BACKGROUND

For microscopic analysis, a few cell types are thin enough to be viewed directly (e.g., algae, protozoa, blood, tissue cultures), but most tissues (e.g., kidney, liver, brain) are too thick to allow light to be transmitted through them. Thus, in order to be examined with a microscope, a specimen must be sufficiently thin to be transparent and must possess sufficient contrast to permit the resolution of structural detail. The tissues can be sliced into very thin sections provided they are first processed to prevent cell damage.

Commonly, two types of procedures are used in preparing specimens of tissue for microscopic examination. In one procedure a specimen is frozen, cut and mounted on a slide in an elapsed time of about 15 minutes. This so-called "frozen section" procedure has the advantage of enabling a rapid histological diagnosis to be made from the specimen, and it is frequently employed in situations where a diagnosis is necessary while a patient is on an operating table. However, the "frozen section" procedure possesses certain disadvantages in that the prepared slide does not possess the uniformity of quality of slides prepared by other methods. Thus, frozen sections are difficult to interpret, and are more likely to be misinterpreted by a pathologist than are usual permanent slides. Further, the process of freezing tissue introduces considerable artifacts in it that can make certain conditions, such as some cancers, impossible to diagnose. Thus, when the frozen section procedure is used in emergency situations, it is customary for another portion of the tissue specimen to be processed using standard fixation/paraffin embedding techniques to have tissue available for additional sections if further examination becomes necessary.

In the other procedures, a slide of relatively high quality is produced when a section of the specimen is chemically fixed and mounted in a block of paraffin. However, using conventional procedures and solutions, the time required to process a specimen of tissue for mounting in paraffin is on the order of many hours to days as compared with the minutes required to process a specimen by the frozen section procedure.

In the preparation of paraffin slides, a specimen of tissue is immersed initially in a fixing agent. The fixed specimen is then immersed in a dehydrating agent, and afterward the specimen is immersed in a clearing agent. Finally, the cleared specimen is immersed in a bath of paraffin which impregnates the specimen and permits it to be sliced into thin sections for subsequent mounting onto slides. Because of the length of time required to prepare specimens by this process, it is customary for hospital laboratories to begin processing the specimens late in the afternoon after surgeons have obtained specimens from their patients. The processing continues through the night, and slides of the specimens are available for microscopic examination the next morning. Although the slides produced according to this procedure are of higher quality than those produced by the frozen section technique, the length of time required to process specimens is too great to enable this procedure to be used in situations where time is of the essence.

Using current procedures, if time or enzyme function is critical frozen sections are the preferred process. If subcellular detail is important, other procedures must be used. Selection of the correct procedure depends on what the cell biologist is looking for and to a point, becomes an art form.

What is needed in the art is a method of fixing tissue which combines the time advantage of the frozen section with the consistency and quality of the traditional paraffin embedded tissue.

SUMMARY OF THE INVENTION

In one aspect, a method of fixing a biological tissue sample is provided. The method includes contacting the tissue sample with a fixing composition comprising about 20-80% v/v DMSO for a time ranging from 10 seconds to 24 hours. The method further includes dehydrating the tissue sample; and clearing the tissue sample. In one embodiment, the sample is contacted with the fixing composition for 30 seconds to 5 minutes. In one embodiment the fixed tissue is then embedded in paraffin, nitrocellulose, plastic or other suitable embedding agent.

In another aspect, a method of fixing a biological tissue sample is provided. The method includes contacting the tissue sample with a dehydration solution composition comprising about 2-80% v/v DMSO for a time ranging from 10 seconds to 24 hours. In one embodiment, the sample is contacted with a series of dehydration solutions containing increasingly higher percentages of alcohol. In one embodiment, the sample is contacted with a solution containing about 50% alcohol and about 50% DMSO. In another embodiment, the sample is then contacted with a solution containing about 98% alcohol and about 2% DMSO. Additional steps may be included between the two previously identified steps. The concentrations discussed below with regard to dehydration solutions are appropriate for use in this embodiment. The method further includes clearing the tissue sample. In one embodiment, the sample is contacted with the dehydration composition for 30 seconds to 5 minutes. In one embodiment, the fixed tissue is contacted with a clearing agent. In another embodiment the fixed tissue is then embedded in paraffin, nitrocellulose, plastic or other suitable embedding agent.

In a further aspect, a method for fixing a tissue sample is provided. The method includes (a) contacting the tissue sample with a fixing composition for about 1 minute to about 5 minutes, the fixing composition comprising about 40% v/v DMSO; about 10% v/v of formalin; and a buffering agent; (b) dehydrating the tissue sample in a non-aqueous solution comprising DMSO and alcohol; and (c) clearing the tissue sample in a clearing solution comprising xylene and DMSO. In one embodiment, the method includes (d) embedding the tissue in paraffin, nitrocellulose, plastic or other suitable material.

In another aspect, a kit for use in preparing tissues is provided. In one embodiment, the kit includes one or more of: a fixative solution, a dehydration solution and a clearing solution. In one embodiment, the fixative solution includes 20-80% DMSO, a fixing agent and a buffering agent. In another embodiment, the dehydration solution includes one or more alcohols and DMSO. In a further embodiment, the clearing solution includes xylene and DMSO. In another embodiment, the kit includes more than one fixative solution, more than one dehydration solution, and/or more than one clearing solution. In a further embodiment, not all of the fixative solution, dehydration solution and clearing solution is present in the kit.

In another aspect, a system for tissue fixing is provided. In one embodiment, the system includes any of the components of the kits described herein, in conjunction with one or more mechanical aids, as further described herein.

Other aspects and advantages of the invention will be readily apparent from the following detailed description of the invention.

DETAILED DESCRIPTION OF THE INVENTION

Figure 1:
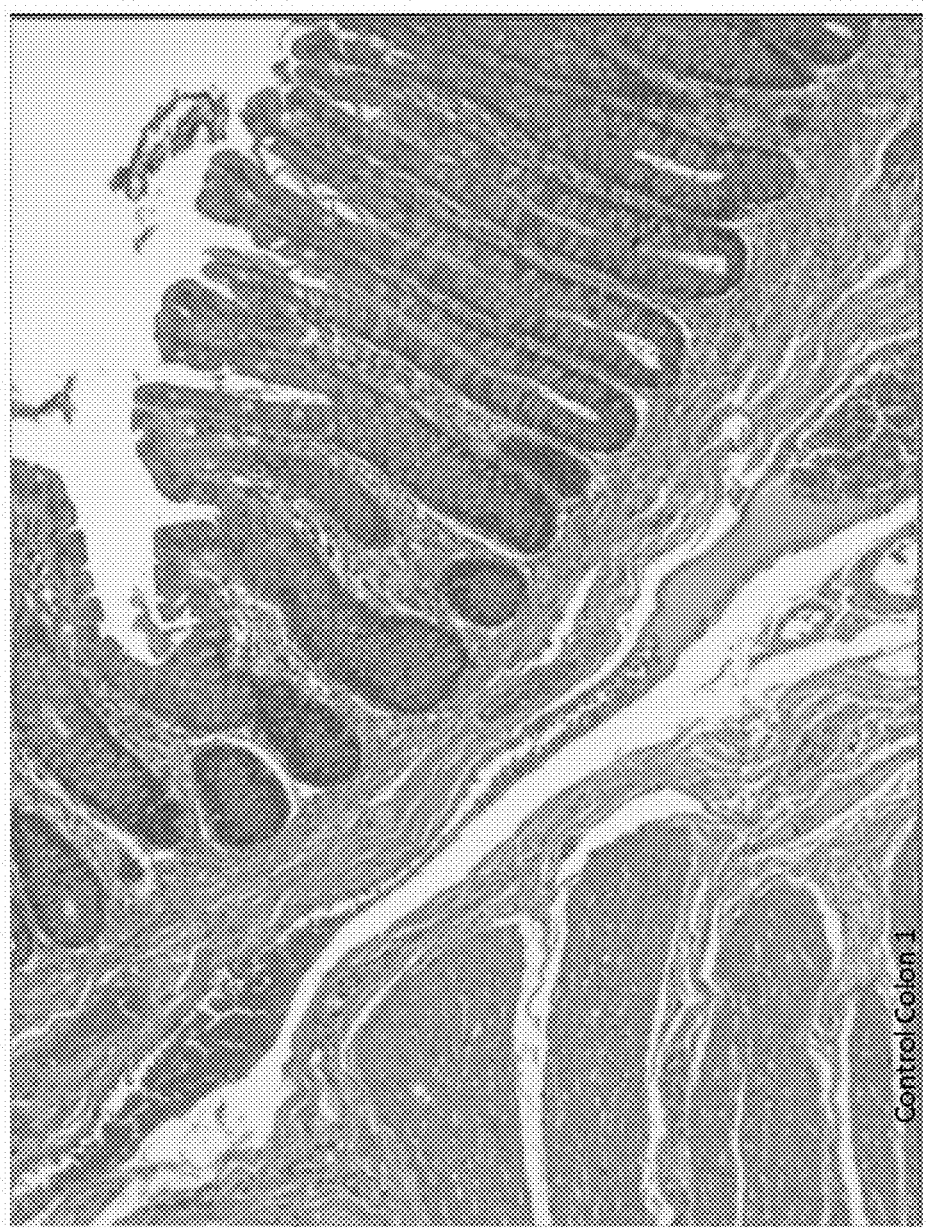
FIG. 1 is a control human colon section prepared according to the method described in Example 3.

It is to be noted that the term "a" or "an" refers to one or more. As such, the terms "a" (or "an"), "one or more," and "at least one" are used interchangeably herein.

While various embodiments in the specification are presented using "comprising" language, under other circumstances, a related embodiment is also intended to be interpreted and described using "consisting of" or "consisting essentially of" language. The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified. Each of the ranges specified herein are inclusive of the endpoints. For example, a range of 20% to 40% includes 20%, 40% and all of the values in between.

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The methods, compositions, kits and systems described herein, provide the ability to produce high quality stained tissue sections at a fraction of the time required for conventional procedures. During cancer surgery, the ability to provide a pathological diagnosis from a stained tissue section will provide the surgeon with information that may be used prior to the patient's departure from the operating room (i.e., intraoperative diagnosis). For example, an indication from the anatomic pathologist that the cancer is confined to the resected tissue may allow the surgeon to be conservative in treatment and to preserve neighboring healthy tissue.

Alternatively, a finding by the anatomic pathologist that cancer is not confined to a resected organ would permit more aggressive surgical treatment while a patient is still in the operating room.

Formalin fixation and paraffin embedding are conventional tissue preservation and processing methods used for histologic diagnosis in over 90% of cases. However, formalin fixation is a slow procedure (approximately 1 h per 1 mm of tissue penetration). Overall, the compositions, methods, systems and kits described herein can provide rapid and improved morphological and molecular preservation to better accommodate both traditional and molecular diagnoses.

Tissue sample

In one embodiment, a method for fixing and stabilizing a cell's native morphology, in a cell containing sample, is provided. The methods, compositions and kits described herein are suitable for use in fixing any desired biological sample which may require stabilization. As used herein, the term "biological sample" may be used interchangeably with "tissue". While, in one embodiment, the methods, compositions, and kits described herein are useful with tissues, such as tissue from a biopsy, it is to be understood that any biological sample which contains cells—whether or not normally classified as a "tissue"—may be fixed using the methods described herein.

In one embodiment, the biological tissue is any tissue that may be fixed using conventional techniques. In another embodiment, the tissue sample is animal or plant tissue. An animal tissue may be derived from a human or non-human animal, including, without limitation, non-human primates, dogs, cats, mice, rats, guinea pigs, fruit flies, and other laboratory animals; farm animals including bovine, ovine, horse, goat, pig, rabbit, etc. In one embodiment, the tissue is from a mammal. In another embodiment, the tissue is from a human. Tissues may be derived from both live and dead sources, e.g., from an autopsy. In another embodiment, the tissue is from an organ, biopsy, circulating tumor cell (CTC), blood sample, plasma sample, serum sample, tissue culture cells, saliva, urine, cerebral spinal fluid, medical sample, egg, embryo, or adult tissue. Tissue samples may be fresh or previously frozen, e.g., those obtained from tissue banks or previously held in storage. Solid tissue may be obtained from surgical biopsy or resection.

Exemplary tissues that may be processed include: appendix, bladder, bone, bowel, brain, breast, carcinoma, cervix (squamous epithelium), gall bladder, heart, kidney, liver, lung, ovary, parotid gland, placenta, prostate, skin, spleen, testicle, thyroid gland, tonsil, and uterus (myometrium and endometrium). Lymphoreticular and fatty tissues may also be processed. Optionally, mineralized tissue may require decalcification prior to processing by the present method. Subsequent analysis may include, without limitation, detecting DNA mutations and RNA expression, genomic analysis, histochemistry, immunochemistry, and proteomic analysis.

Any size tissue sample may be processed using the methods, compositions and kits described herein. Processing times may vary based, in part, on the size of the sample. In one embodiment, the tissue sample is about 0.1 to about 2.0 cm in size, or fractions or integers therebetween. In another embodiment, the tissue sample is about 1 to about 5 mm in size, or fractions or integers therebetween. In another embodiment, the tissue sample is about 1 mm. In another embodiment, the tissue sample is about 2 mm. In another embodiment, the tissue sample is about 3 mm. In another embodiment, the tissue sample is about 4 mm. In another embodiment, the tissue sample is about 5 mm. In another embodiment, the tissue sample is about 6 mm. In another embodiment, the tissue sample is about 7 mm. In another embodiment, the tissue sample is about 8 mm. In another embodiment, the tissue sample is about 9 mm. In another embodiment, the tissue sample is about 10 mm.

Fixing

In one aspect, a method of fixing biological tissue is provided. In one embodiment, a fixing solution is use which contains from about 20% to about 80% dimethyl sulfoxide (DMSO). The methods and kits provided herein are based on, in part, that relatively high concentrations of DMSO, when included in a fixing solution, allow the fixative to penetrate much more rapidly than without DMSO. This provides significantly faster processing times for fixing biological tissues. Further, the inclusion of DMSO helps increase the strength and speed of crosslinking of proteins, when used with an additive fixing agent, and provide clear, consistent specimens for imaging.

In one embodiment, the fixing solution includes about 20% to about 80% DMSO, inclusive of the endpoints. In yet another embodiment, the fixing solution includes about 30% to about 60% DMSO. In another embodiment, the fixing solution includes about 40% to about 50% DMSO. In yet another embodiment, the fixing solution includes about 20%, 25%, 30%, 35%, 40%, 45%, 50%, 55%, 60%, 65%, 70%, 75%, or about 80% DMSO. The DMSO used may be of commercial grade, e.g., about 95% or greater purity. In one embodiment, the DMSO is of about 99% or greater purity.

In another embodiment, the fixing solution further includes one or more fixing agents. In one embodiment, the fixing solution includes two fixing agents. In one embodiment, the fixing solution includes three fixing agents. In one embodiment, the fixing solution includes four fixing agents. In one embodiment, the fixing solution includes five or more fixing agents. The fixing agent may be any chemical fixative, many of which are known in the art. See, e.g., Kiernan, Histological and Histochemical Methods, $4^{th}$ Ed., Scion Publishing 2008, which is incorporated herein by reference. In one embodiment, the fixing agent is formaldehyde. In another embodiment, the fixing agent includes formalin. A saturated water solution, of about 40% formaldehyde by volume or 37% by mass, is called "100% formalin". A small amount of stabilizer, such as methanol, may be added to suppress oxidation and polymerization. A typical commercial grade formalin may contain about 10-12% methanol in addition to various metallic impurities. A commercial grade formalin solution may also be buffered. In one embodiment, the formalin solution contains sodium phosphate, monobasic and/or sodium phosphate, dibasic.

Common fixative agents which are useful in the invention include, without limitation, formaldehyde, formalin, paraformaldehyde, gluteraldehyde, other aldehydes including chloral hydrate, acrolein, hydroxyaldipaldehyde, crotonaldehyde and glyoxal; organic coagulants including alcohols including ethanol and methanol; acetone; tricholoroacetic acid; mercuric chloride; zinc salts including zinc chloride; mercuric chloride; picric acid; acetic acid; chromium compounds including chromium trioxide and potassium dichromate; osmium tetroxide; and ruthenium tetroxide. Other fixative agents useful in the invention include mineral acids that serve as coagulants; metal ions and complexes that cause precipitation of proteins; iodine; organic protein coagulants including p-toluenesulphonic acid and tannic acid; surfactants; cationic dyes; bifunctional organic compounds; and sodium periodate. Other non-formalin based commercially available fixative agents include FineFIX, RCL2, and HOPE-in.

The selection of the fixing agent may be determined by the person of skill in the art based on the desired structural or chemical components and the end use of the fixed tissue sample. Often a mixture of different fixing agents is employed in order to offset undesirable effects of individual substances and to obtain more than one type of chemical fixation. In one embodiment, acetic acid may be included in the fixative solution to preserve chromosomes, to precipitate chromatin of interphase nuclei, and to oppose the shrinking actions of other agents such as ethanol and picric acid.

The concentration of the fixing agent will be determined based on the selection of the agent and the end use of the fixed tissue sample, and ranges from about 0.25% (for gluteraldehyde) to up to about 80% (for alcohols). In one embodiment, the fixative is formaldehyde. In another embodiment, the formaldehyde includes about 2% to 10% of the fixing solution. In one embodiment, the fixative includes about 5 to about 20% formalin. In one embodiment, the fixative includes about 10% formalin. In one embodiment, the fixative includes about 5% formalin. In one embodiment, the fixative includes about 15% formalin. In one embodiment, the fixative includes about 5, 6, 7, 8, 9, 10, 11, 12, 13, 14, 15, 16, 17, 18, 19, or 20% formalin. In another embodiment, the fixative is an alcohol. In one embodiment, the fixative is ethanol, methanol, or isopropanol, or combinations thereof. In one embodiment, the fixative is a combination of ethanol, methanol, and isopropanol. In another embodiment, the alcohol or mixture thereof includes about 30% to about 80% of the fixing solution. In another embodiment, the fixative is acetone. In another embodiment, the acetone includes about 30% to about 80% of the fixing solution. In another embodiment, the fixative is gluteraldehyde. In another embodiment, the gluteraldehyde includes about 0.25% to about 4% of the fixing solution. In another embodiment, the fixative is glyoxal. The concentration of the fixing agent can be determined by the person of skill in the art.

In one embodiment, the fixing solution includes more than one fixing agent. Specific combinations of fixing agents are known in the art and may be selected by the person of skill in the art. Some combinations known in the art, which are useful in the invention, include without limitation: ethanol and glacial acetic acid; ethanol, chloroform, and glacial acetic acid; ethanol, formalin, and glacial acetic acid; formalin and sodium chloride; neutral buffered formalin; formaldehyde and gluteraldehyde; formalin and calcium acetate; formalin and zinc sulfate; picric acid, formalin and glacial acetic acid; picric acid, formalin, ethanol, ethyl acetate, and glacial acetic acid; mercuric chloride, sodium chloride, trichloroacetic acid, formalin and glacial acetic acid; mercuric chloride, potassium dichromate, and sodium sulfate, optionally with formalin and/or glacial acetic acid; osmium tetroxide and potassium dichromate, optionally with glacial acetic acid; osmium tetroxide and mercuric chloride; paraformaldehyde and picric acid; lysine monohydrochloride, sodium phosphate, paraformaldehyde and sodium metaperiodate or sodium paraperiodate; calcium acetate, zinc acetate and zinc chloride. Other combinations of the above-identified fixatives and others are also contemplated for use in the invention.

The fixative solution may also include one or more additional components. In one embodiment, the fixative solution includes one or more buffering agents. Suitable buffers include those that maintain the pH of the fixing solution in the range of about 4 to about 9. In one embodiment, the fixing solution is maintained at a physiological pH. In one embodiment, a pH in the range of about 7 to about 8 is obtained. In another embodiment, the fixing solution is about pH 7.4. The buffering agent may be organic or non-organic, based upon the composition of the remainder of the fixing composition. Fixing compositions comprising about 40 to about 45% or greater DMSO may require an organic buffering agent, although this can be readily determined by one of skill in the art. Organic buffering agents known in the art and useful in the invention include, without limitation, HEPES (4-(2-hydroxyethyl)-1-piperazineethanesulfonic acid), MOPS (3-(N-morpholino)propanesulfonic acid), PIPES (piperazine-N,N'-bis(2-ethanesulfonic acid)), MES (2-(N-morpholino)ethanesulfonic acid), and TRIS, also known as THAM (tris(hydroxymethyl)aminomethane)). Non-organic buffering agents known in the art and useful in the invention include, without limitation, potassium hydrogen phthalate, borax, boric acid, sodium acetate, HCl, acetic acid, disodium hydrogen phosphate, sodium dihydrogen phosphate, potassium dihydrogen phosphate, citric acid, sodium citrate, sodium cacodylate, barbitone sodium, blycine, sodium hydroxide, sodium carbonate, and sodium bicarbonate.

In one embodiment, the fixing solution may include one or more of the components listed as clearing agents, as further described below. In one embodiment, the fixing solution includes xylene or a xylene substitute. In another embodiment, the fixing solution includes naphtha.

The fixing solution may further contain one or more salts including sodium chloride, potassium chloride, calcium chloride, magnesium chloride, and the like. In addition, in one embodiment, the fixing solution includes one or more solvent. The solvent may be water, saline, phosphate buffered saline, Ringer's solution, etc., or combinations thereof In one embodiment, the fixing solution includes about 4% to about 10% formaldehyde, about 40% to about 50% DMSO, water, and a buffering agent. In one embodiment, the buffering agent includes one or more of sodium phosphate, monobasic and sodium phosphate, dibasic. In another embodiment, the buffer includes tetrapropyl ammonium phosphate.

In the method of fixing described herein, the tissue may be fixed for a time ranging from about 10 seconds to about 24 hours. The duration of the fixing step will be determined based on the size of the tissue sample, the fixing solution used, the temperature and whether or not any mechanical aids are used. In another embodiment, the fixing step is about 20 seconds. In another embodiment, the fixing step is about 30 seconds. In another embodiment, the fixing step is about 40 seconds. In another embodiment, the fixing step is about 50 seconds. In another embodiment, the fixing step is about 1 minute. In another embodiment, the fixing step is about 75 seconds. In another embodiment, the fixing step is about 90 seconds. In another embodiment, the fixing step is about 105 seconds. In another embodiment, the fixing step is about 2 minutes. In another embodiment, the fixing step is about 2 minutes and 30 seconds. In another embodiment, the fixing step is about 2 minutes and 45 seconds. In another embodiment, the fixing step is about 3 minutes. In another embodiment, the fixing step is about 3 minutes and 15 seconds. In another embodiment, the fixing step is about 3 minutes and 30 seconds. In another embodiment, the fixing step is about 3 minutes and 45 seconds. In another embodiment, the fixing step is about 4 minutes. In another embodiment, the fixing step is about 4 minutes and 30 seconds. In another embodiment, the fixing step is about 5 minutes. In another embodiment, the fixing step is about 5 minutes and 30 seconds. In another embodiment, the fixing step is about 6 minutes. In another embodiment, the fixing step is about 6 minutes and 30 seconds. In another embodiment, the fixing step is about 7 minutes. In another embodiment, the fixing step is about 7 minutes and 30 seconds. In another embodiment, the fixing step is about 8 minutes. In another embodiment, the fixing step is about 8 minutes and 30 seconds. In another embodiment, the fixing step is about 9 minutes. In another embodiment, the fixing step is about 9 minutes and 30 seconds. In another embodiment, the fixing step is about 10 minutes. In yet another embodiment, the fixing step is 11, 12, 13, 14, 15, 16, 17, 18, 19 or 20 minutes. In yet another embodiment, the fixing step is 20, 25, 30, 35, 40, 45, 50, 55 or 60 minutes. In yet another embodiment, the fixing step is 1, 2, 3, 4, 5, 6, 7, 8, 9, 10, 11, 12, 13, 14, 15, 16, 17, 18, 19, 20, 21, 22, 23 or 24 hours.

In one embodiment, the "fixing step" as described above, is performed using an alcohol as the fixing agent. Thus, it can be said that, in that embodiment, the fixing step is skipped and dehydration is the first step of the method. In this embodiment, it is appropriate that any of the dehydration solutions/steps described herein may be used as the "fixing" step/agent. In one embodiment, the dehydration includes about 2% to about 60% DMSO.

Decalcification

In one embodiment, the tissue is decalcified after fixing. The tissue may be decalcified by acid or chelating agent. For acid decalcification the choice of acid may be selected from those known in the art. Known decalcifying acids include, without limitation, formic acid, De Castro's fluid (nitric acid), ascorbic acid, acetic acid. For decalcification by chelation, EDTA is used. In one embodiment, disodium EDTA is used. In another embodiment, ammonium EDTA is used.

Hard specimens cannot be sectioned with an ordinary microtome, but they can be softened after fixation, usually by removing the substances responsible for the hardness of the tissue. Decalcification is the chemical dissolution of insoluble calcium salts with a suitable acid or chelating agent. Other approaches are available for softening hard materials that contain silica or which owe their hardness to compact organic materials. Alternatively, hard tissues can be cut with a special microtome, which is equipped with a chisel-shaped knife of hardened steel.

Dehydration

In one embodiment, the tissue is dehydrated after fixing, after decalcification, or both. A biological tissue specimen may be embedded in paraffin once it has been equilibrated with a solvent that is miscible with wax. This is typically accomplished by replacing the water in the specimen, first with alcohol and then with a paraffin solvent (clearing agent).

In one embodiment of the methods described herein, the dehydration solution includes DMSO. DMSO may be present in the dehydration solution from an amount of about 1% to about 60%. In one embodiment, the dehydration solution includes about 2% to about 30% DMSO. In another embodiment, the dehydration solution includes about 5% DMSO. In another embodiment, the dehydration solution includes about 10% DMSO. In another embodiment, the dehydration solution includes about 15% DMSO. In another embodiment, the dehydration solution includes about 20% DMSO. In another embodiment, the dehydration solution includes about 25% DMSO. In another embodiment, the dehydration solution includes about 30% DMSO. In another embodiment, the dehydration solution includes about 35% DMSO. In another embodiment, the dehydration solution includes about 40% DMSO. In another embodiment, the dehydration solution includes about 45% DMSO. In another embodiment, the dehydration solution includes about 50% DMSO. In another embodiment, the dehydration solution includes about 55% DMSO. In another embodiment, the dehydration solution includes about 60% DMSO. In yet another embodiment, the dehydration solution includes about 2, 3, 4, 5, 6, 7, 8, 9, 10, 11, 12, 13, 14, 15, 16, 17, 18, 19, 20, 21, 22, 23, 24, 25, 26, 27, 28, 29, or 30% DMSO. In yet another embodiment, the dehydration solution includes about 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60% DMSO.

In one embodiment, the dehydration step is performed in a non-aqueous solution comprising DMSO. The non-aqueous solution may include more than one component. In one embodiment, the non-aqueous solution includes one or more alcohols. The alcohol, in one embodiment, is ethanol, isopropanol, methanol, or combinations thereof. In another embodiment, the non-aqueous solution includes acetone. In another embodiment, the non-aqueous solution includes one or more alcohol.

In one embodiment of the invention, the dehydration step includes multiple steps, each successive step comprising contacting the sample with a higher percentage of alcohol. For example, in one embodiment, the dehydration solution of includes three separate solutions: (i) about 70% alcohol and about 30% DMSO; (ii) about 95% alcohol and about 5% DMSO; and (iii) about 98% alcohol and about 2% DMSO. In one embodiment, the sample is contacted with the first dehydration solution for a period of time; then the sample is contacted with the second dehydration solution for a second period of time; then the sample is contacted with the third dehydration solution for a third period of time.

In the methods described herein, the tissue may be dehydrated for a time ranging from about 10 seconds to about 24 hours. The duration of the dehydration step(s) will be determined based on the size of the tissue sample, the dehydration solution used, the temperature and whether or not any mechanical aids are used. The duration of each dehydration step, if applicable, may be individually selected. In one embodiment, the dehydration step is about 20 seconds. In another embodiment, the dehydration step is about 30 seconds. In another embodiment, the dehydration step is about 40 seconds. In another embodiment, the dehydration step is about 50 seconds. In another embodiment, the dehydration step is about 1 minute. In another embodiment, the dehydration step is about 75 seconds. In another embodiment, the dehydration step is about 90 seconds. In another embodiment, the dehydration step is about 105 seconds. In another embodiment, the dehydration step is about 2 minutes. In another embodiment, the dehydration step is about 2 minutes and 30 seconds. In another embodiment, the dehydration step is about 2 minutes and 45 seconds. In another embodiment, the dehydration step is about 3 minutes. In another embodiment, the dehydration step is about 3 minutes and 15 seconds. In another embodiment, the dehydration step is about 3 minutes and 30 seconds. In another embodiment, the dehydration step is about 3 minutes and 45 seconds. In another embodiment, the dehydration step is about 4 minutes. In another embodiment, the dehydration step is about 4 minutes and 30 seconds. In another embodiment, the dehydration step is about 5 minutes. In another embodiment, the dehydration step is about 5 minutes and 30 seconds. In another embodiment, the dehydration step is about 6 minutes. In another embodiment, the dehydration step is about 6 minutes and 30 seconds. In another embodiment, the dehydration step is about 7 minutes. In another embodiment, the dehydration step is about 7 minutes and 30 seconds. In another embodiment, the dehydration step is about 8 minutes. In another embodiment, the dehydration step is about 8 minutes and 30 seconds. In another embodiment, the dehydration step is about 9 minutes. In another embodiment, the dehydration step is about 9 minutes and 30 seconds. In another embodiment, the dehydration step is about 10 minutes. In yet another embodiment, the dehydration step is 11, 12, 13, 14, 15, 16, 17, 18, 19 or 20 minutes. In yet another embodiment, the dehydration step is 20, 25, 30, 35, 40, 45, 50, 55 or 60 minutes. In yet another embodiment, the dehydration step is 1, 2, 3, 4, 5, 6, 7, 8, 9, 10, 11, 12, 13, 14, 15, 16, 17, 18, 19, 20, 21, 22, 23 or 24 hours. If the dehydration step includes more than one step, each step may be equal or different in duration.

Clearing

In one embodiment, the fixed tissue is contacted with a clearing solution which includes a solvent which is miscible with the embedding agent. Xylene is useful in the methods described herein and is miscible with paraffin. Xylene (or xylenes) is the common name for the chemical dimethylbenzene. In one embodiment, xylene may be a mixture of the three isomers 1,2-dimethylbenzene (o-xylene), 1,3-dimethylbenzene (m-xylene) and 1,4-dimethylbenzene (p-xylene). Laboratory-grade xylene may contain m-xylene (about 40 to about 65%), p-xylene (about 20%), o-xylene (about 20%) and ethyl benzene (about 6 to 20%) and, optionally, traces of toluene, trimethyl benzene, phenol, thiophene, pyridine and hydrogen sulfide. Xylene containing other ratios of the three isomer forms is also useful herein. Reagent-grade xylene is also useful herein. Other clearing agents useful herein include, without limitation, benzene, choloroform, toluene and mixtures thereof. Other clearing agents include 'xylene substitutes', including D-, L- and DL-limonene. Other clearing agents include amyl acetate, n-butanol, carbon tetrachloride, cedarwood oil, white oil, n-heptane, benzyl benzoate, methyl benzoate, methyl siacylate, terpineol, methyl chloroform and mixtures thereof. Additional clearing agents include t-butanol, dioxane, dimethyl sulfoxinde, THF and mixtures thereof. Further clearing agents include proprietary solutions including HistoChoice® clearing agent, XS-3™, ClearRite™, Clearify™, etc. The clearing agent may include combinations of any of the listed agents.

In one embodiment, the clearing solution includes DMSO. DMSO may be present in the clearing solution from an amount of about 2% to about 20%. In one embodiment, the clearing solution includes about 10% DMSO. In one embodiment, the clearing solution includes about 2% to DMSO. In another embodiment, the clearing solution includes about 3% DMSO. In another embodiment, the clearing solution includes about 4% DMSO. In another embodiment, the clearing solution includes about 5% DMSO. In one embodiment, the clearing solution includes about 6% to DMSO. In another embodiment, the clearing solution includes about 7% DMSO. In another embodiment, the clearing solution includes about 8% DMSO. In another embodiment, the clearing solution includes about 9% DMSO. In one embodiment, the clearing solution includes about 11% to DMSO. In another embodiment, the clearing solution includes about 12% DMSO. In another embodiment, the clearing solution includes about 13% DMSO. In another embodiment, the clearing solution includes about 14% DMSO. In one embodiment, the clearing solution includes about 15% to DMSO. In another embodiment, the clearing solution includes about 16% DMSO. In another embodiment, the clearing solution includes about 17% DMSO. In another embodiment, the clearing solution includes about 18% DMSO. In one embodiment, the clearing solution includes about 19% to DMSO. In another embodiment, the clearing solution includes about 20% DMSO.

In one embodiment, the clearing step includes multiple steps. In each step, the composition of the clearing solution may be individually determined. In one embodiment, the clearing step includes contacting the sample with a solution comprising xylene and DMSO.

In one embodiment, the dehydration and clearing steps are combined. In another embodiment, the dehydration and clearing steps are alternated. For example, in one embodiment, the clearing step includes contacting the sample with the following solutions: (i) about 98% xylene and about 2% DMSO; (ii) about 95% alcohol and about 5% DMSO; (iii) about 98% xylene and about 2% DMSO.

In one embodiment, the method for fixing a tissue sample includes:
(a) contacting the tissue sample with a fixing composition for about 1 minute to about 5 minutes, the fixing composition comprising about 40% v/v DMSO; about 10% v/v of formalin; and a buffering agent;
(b) dehydrating the tissue sample in a non-aqueous solution comprising DMSO and alcohol;
(c) clearing the tissue sample in a clearing solution comprising xylene and DMSO; and
(d) infiltrating with and embedding the tissue in paraffin, nitrocellulose, plastic or other suitable material.

Temperature

When the temperature of a fixative is raised or lowered, the rate of diffusion into the specimen is affected, as is the rate of the chemical fixation reactions occurring with the various tissue components. Increasing temperature accelerates the process of fixation. Excessive heat however, particularly if it is prolonged, can damage cells and cause substantial shrinkage and hardening of the specimen. Another issue with using hot fixative solutions to initially fix larger specimens (greater than 3 mm thick), is that the outside of the specimen fixes rapidly whilst it may take quite some time for the fixative to penetrate to the center of the block and this area may be poorly fixed or not fixed at all. Thus, the temperature at which the methods described herein are performed, may be selected by the person of skill in the art based on the desired speed, size of the specimen, etc.

The methods described herein may be performed at any temperature in which the reagents (in combination) remain in liquid form. For example, although the freezing point of DMSO is relatively high at about 18.5° C., when in combination with other reagents, the solutions are useful at temperatures below this point. In one embodiment, any of the steps described herein are performed at a temperature from 0° C. to about 80° C. The temperature at which each step is performed may be selected individually for that step. In one embodiment, the method is performed at room temperature In another embodiment, the steps are performed at about 37° C. to about 45° C. In another embodiment, the steps are performed at about 40 to about 55° C. In yet another embodiment, the steps are performed at about 46° C.

Mechanical aids

Various mechanical aids are known in the art which may aid in the overall fixation process, including any of the steps herein described. Mechanical aids useful herein include, without limitation, microwave, ultrasound, vacuum, agitation, electrophoresis, centrifuge, and automated tissue processors. Microwaves are a form of non-ionizing radiation produced by the magnetron in domestic and scientific microwave ovens. At a frequency of 2.5 GHz, they have the capacity to generate instantaneous heat when dipolar molecules such as water or polar side chains of proteins are exposed to their alternating magnetic fields at 2.5 billion cycles per second. The rate at which the microwave energy will generate heat during tissue fixation depends on a number of factors including the power setting and power output of the oven, the volume and nature of the holding solution, the composition, shape and number of containers (including cassettes), the agitation or movement of the containers, and the number, volume and dimensions of the specimens being fixed. Thus, the use of microwaves will result in shorter fixation times. In conjunction with the method and compositions described herein, the use of microwave technology can further speed the fixation process.

In one embodiment, a microwave is used in any of the methods described herein. For example, tissue specimens in a DMSO containing fixative solution described herein may be microwaved to assist the fixative action of the fixing agent (referred to as "microwave-assisted fixation"). In one embodiment, the microwaving may be carried out while the tissue is in fixative, in which case there may be some hazard from toxic fumes produced, or the tissue may be transferred to saline or buffer for the microwave step. In this embodiment, the use of fixatives of relatively low toxicity containing glyoxal, are useful in the methods described herein. In one embodiment, the tissue sample is contacted with a fixing composition containing about 20 to about 80% v/v DMSO, as described herein. The tissue sample is then microwaved for about 5 seconds to about 5 minutes. In one embodiment, the sample is microwaved in the fixative. In another embodiment, the sample is transferred to a buffer or saline solution prior to microwaving. In one embodiment, the tissue sample is microwaved for about 10 seconds. In another embodiment, the tissue sample is microwaved for about 15 seconds. In another embodiment, the tissue sample is microwaved for about 20 seconds. In another embodiment, the tissue sample is microwaved for about 25 seconds. In another embodiment, the tissue sample is microwaved for about 30 seconds. In another embodiment, the tissue sample is microwaved for about 40 seconds. In another embodiment, the tissue sample is microwaved for about 50 seconds. In another embodiment, the tissue sample is microwaved for about 60 seconds. In another embodiment, the tissue sample is microwaved for about 75 seconds. In another embodiment, the tissue sample is microwaved for about 90 seconds. In another embodiment, the tissue sample is microwaved for about 2 minutes. In another embodiment, the tissue sample is microwaved for about 2.5 minutes. In another embodiment, the tissue sample is microwaved for about 3 minutes. In another embodiment, the tissue sample is microwaved for about 3.5 minutes. In another embodiment, the tissue sample is microwaved for about 4 minutes. In another embodiment, the tissue sample is microwaved for about 4.5 minutes.

Ultrasound technology may also be employed in conjunction with any of the methods described herein. The critical factors for consistent ultrasound-facilitated processing without tissue damage are maintaining ultrasound at a high frequency (>0.1 MHz) and high intensity (1-20 W/cm2) and controlling the total energy received by the tissue See, e.g., Wang et al, Ultrasound Facilitated Formalin-fixed and Paraffin-embedded Tissue Specimen Preparation Technology, 2008 BRN Symposium Poster available at biospecimens.cancer.gov/meeting/brnsymposium/docs/2008pres/Poster27-Wang.pdf, which is incorporated by reference herein. Applying high-frequency, high-intensity ultrasound to the fixative cuts fixation time. The intensity of ultrasound used depends on the particular procedure and will be in the range of about 0.001-20 W/cm2. See, e.g., U.S. Pat. No. 6,291,180, which is incorporated by reference herein. Fixation of various tissues such as lymph node, brain, breast, and prostate suggests that, compared to the conventional method, implementation of ultrasound retains superior and more uniform tissue morphology preservation. Less protein antigenicity is altered so that rapid immunohistochemical reactions occur with higher sensitivity and intensity, reducing the need for antigen retrieval pretreatment. Better RNA preservation results in stronger signals in in situ hybridization and longer RNA fragments extracted from fixed tissues, probably due to rapid inhibition of endogenous RNase activity. See, Chu et al, Ultrasound-accelerated formalin fixation of tissue improves morphology, antigen and mRNA preservation, Modern Pathology (2005) 18, 850-863, advance online publication, 17 Dec. 2004, which is incorporated by reference herein. The use of ultrasound in conjunction with the methods described herein can be readily accomplished by one of skill in the art. In one embodiment, ultrasound is used in conjunction with microwave technology in the methods described herein.

In one embodiment, the tissue sample is contacted with a fixing composition containing about 20 to about 80% v/v DMSO, as described herein. The tissue sample is then subject to high intensity, high frequency ultrasound for about 5 seconds to about 15 minutes. In one embodiment, the sample is subject to ultrasound while in the fixative. In another embodiment, the sample is transferred to a buffer or saline solution prior to ultrasound. In one embodiment, the tissue sample is subject to ultrasound for about 10 seconds. In another embodiment, the tissue sample is subject to ultrasound for about 15 seconds. In another embodiment, the tissue sample is subject to ultrasound for about 20 seconds. In another embodiment, the tissue sample is subject to ultrasound for about 25 seconds. In another embodiment, the tissue sample is subject to ultrasound for about 30 seconds. In another embodiment, the tissue sample is subject to ultrasound for about 40 seconds. In another embodiment, the tissue sample is subject to ultrasound for about 50 seconds. In another embodiment, the tissue sample is subject to ultrasound for about 60 seconds. In another embodiment, the tissue sample is subject to ultrasound for about 75 seconds. In another embodiment, the tissue sample is subject to ultrasound for about 90 seconds. In another embodiment, the tissue sample is subject to ultrasound for about 2 minutes. In another embodiment, the tissue sample is subject to ultrasound for about 2.5 minutes. In another embodiment, the tissue sample is subject to ultrasound for about 3 minutes. In another embodiment, the tissue sample is subject to ultrasound for about 3.5 minutes. In another embodiment, the tissue sample is subject to ultrasound for about 4 minutes. In another embodiment, the tissue sample is subject to ultrasound for about 4.5 minutes. In another embodiment, the tissue sample is subject to ultrasound for about 5 minutes. In another embodiment, the tissue sample is subject to ultrasound for about 6 minutes. In another embodiment, the tissue sample is subject to ultrasound for about 7 minutes. In another embodiment, the tissue sample is subject to ultrasound for about 8 minutes. In another embodiment, the tissue sample is subject to ultrasound for about 9 minutes. In another embodiment, the tissue sample is subject to ultrasound for about 10 minutes. In another embodiment, the tissue sample is subject to ultrasound for about 11 minutes. In another embodiment, the tissue sample is subject to ultrasound for about 12 minutes. In another embodiment, the tissue sample is subject to ultrasound for about 13 minutes. In another embodiment, the tissue sample is subject to ultrasound for about 14 minutes. In another embodiment, the tissue sample is subject to ultrasound for about 15 minutes.

The methods described herein may also utilize an automated tissue processor. There are two main types of processors, the tissue-transfer (or "dip and dunk") machines where specimens are transferred from container to container to be processed, or the fluid-transfer (or "enclosed") types where specimens are held in a single process chamber or retort and fluids are pumped in and out as required. Most modern fluid-transfer processors employ raised temperatures, effective fluid circulation and incorporate vacuum/pressure cycles to enhance processing and reduce processing times.

In one embodiment, an automated tissue processor is used with the fixative, dehydration, and/or clearing solutions described herein. In another embodiment, the methods described herein are carried out using an automated tissue processor.

Various automated tissue processors which are useful with the methods described herein, are known in the art. Some exemplary proprietary processors include TissueWave™ Microwave Processor, Excelsior™ AS Tissue Processor, STP 120 Spin Tissue Processor, all from Thermo Scientific; Tissue Processing; Leica ASP6025, Leica PELORIS II, Leica RemoteCare, Leica ASP300 S, Leica ASP200 S, and Leica TP1020, all from Leica Biosystems; LYNX II from Electron Microscopy Sciences, etc. Other systems are known in the art and are equally useful herein.

Kits

In another aspect of the invention, a kit for use in preparing specimens is provided. In one embodiment, the kit includes any of the components described herein. In another embodiment, the kit contains one or more of the following components: (a) a fixative solution comprising about 20 to about 80% DMSO, a fixing agent and a buffering agent; (b) a dehydration solution comprising one or more alcohols and DMSO; and (c) a clearing solution comprising xylene and DMSO. In another embodiment, the kit includes more than one of component (a) and/or more than one of component (b) and/or more than one of component (c). In one embodiment, the fixative agent is formaldehyde (formalin), gluteraldehyde, glyoxal or alcohol. In another embodiment, the kit includes more than one dehydration solution, each solution comprising a different percentage of alcohol. In one embodiment, the fixative solution of (a) includes about 40% DMSO.

In another embodiment, the kit provided herein includes (a) a fixative solution comprising about 40% DMSO, a fixing agent and a buffering agent; (b) a dehydration solution comprising one or more alcohol and DMSO; and (c) a clearing solution comprising xylene and DMSO. In one embodiment, the dehydration solution of (b) includes multiple solutions, each solution comprising a different percentage of alcohol. In another embodiment, the dehydration solution of (b) includes: (i) about 70% alcohol and about 30% DMSO; (ii) about 95% alcohol and about 5% DMSO, and (iii) about 98% alcohol and about 2% DMSO.

In another embodiment, the kit includes one or more components necessary for embedding the tissue in paraffin, nitrocellulose, plastic or other suitable embedding agent.

In addition to the above components, the kit may include vessels for collecting the specimen, instructions, various tubes, etc.

The methods, solutions, and kits described herein are suitable for use with any commonly used or commercially available immunohistochemistry methods/kits. The sections produced as described herein may be stained according to standard protocols, using standard reagents. The sections produced according to the invention are of equal or superior quality to sections produced according to commonly used fixation methods.

The following examples are illustrative only and are not intended to limit the present invention.

EXAMPLES

Example 1

Samples Fixed According to One Embodiment of the Method of the Invention

The following biopsy tissue samples were obtained: human colon, human lung, human fatty liver, human spleen, human heart, mouse smooth muscle, mouse liver, mouse heart, mouse skeletal muscle, mouse lung, mouse kidney, human lymphoma Tissue samples approximately 2 mm in size were processed according to the following protocol, at 46° C.:

1 minute in a fixing solution containing 10% v/v formalin (buffered with sodium phosphate, monobasic and/or sodium phosphate, dibasic), 40% DMSO in water. 1 minute in a dehydration solution containing 70% alcohol and 30% DMSO. 1 minute in a dehydration solution containing 95% alcohol and 5% DMSO. 1 minute in a dehydration solution containing 98% alcohol and 2% DMSO. 1 minute in a clearing solution containing 90% xylene and 10% DMSO. 1 minute in a dehydration solution containing 98% alcohol and 2% DMSO. 1 minute in a clearing solution containing 90% xylene and 10% DMSO.

The samples were then infiltrated with paraffin for 15 minutes at about 60° C. The samples were then embedded in paraffin according to standard protocols. The samples were sectioned on a Manual Rotary Microtome for Routine Sectioning (Thermo Scientific™ HM 325) to a thickness of 4 μM. Sections were de-paraffinized and stained using standard immunohistochemical techniques (e.g., haematoxylin and eosin stain).

In brief, the de-paraffinizing and staining protocol were as follows:
1. xylene—6 min;
2. alcohol (ethanol) 100%—60 sec;
3. alcohol (ethanol) 95%—30 sec;
4. rinse with water—60 sec;
5. Hematoxylin—60 sec;
6. rinse with water—90 sec;
7. alcohol (ethanol) 95%—30 sec;
8. Eosin—30 sec;
9. alcohol (ethanol) 95%—10 sec;
10. alcohol (ethanol) 100%—90 sec;
11. Xylene—60 sec.

Samples were coverslipped and viewed under a microscope. Slides were found to be comparable to slides prepared according to commonly used procedures (data not shown).

Example 2

Samples Fixed According to One Embodiment of the Method of the Invention

Tissue samples approximately 4 mm in size were fixed and processed according to the following protocol, at 46° C.:

2.5 minute in a fixing solution containing 10% v/v formalin (buffered with sodium phosphate, monobasic and/or sodium phosphate, dibasic), 40% DMSO in water. 2.5 minutes in a dehydration solution containing 70% alcohol and 30% DMSO. 2.5 minutes in a dehydration solution containing 95% alcohol and 5% DMSO. 2.5 minutes in a dehydration solution containing 98% alcohol and 2% DMSO. 2.5 minutes in a clearing solution containing 90% xylene and 10% DMSO. 2.5 minutes in a dehydration solution containing 98% alcohol and 2% DMSO. 2.5 minutes in a clearing solution containing 90% xylene and 10% DMSO.

The samples were then infiltrated with paraffin for 15 minutes at about 60° C. The samples were then embedded in paraffin according to standard protocols. The samples were sectioned on a Manual Rotary Microtome for Routine Sectioning (Thermo Scientific™ HM 325) to a thickness of 4 µM. Sections were de-paraffinized as described in Example 2 and stained using standard immunohistochemical techniques (e.g., haematoxylin and eosin stain).

Figure 5:
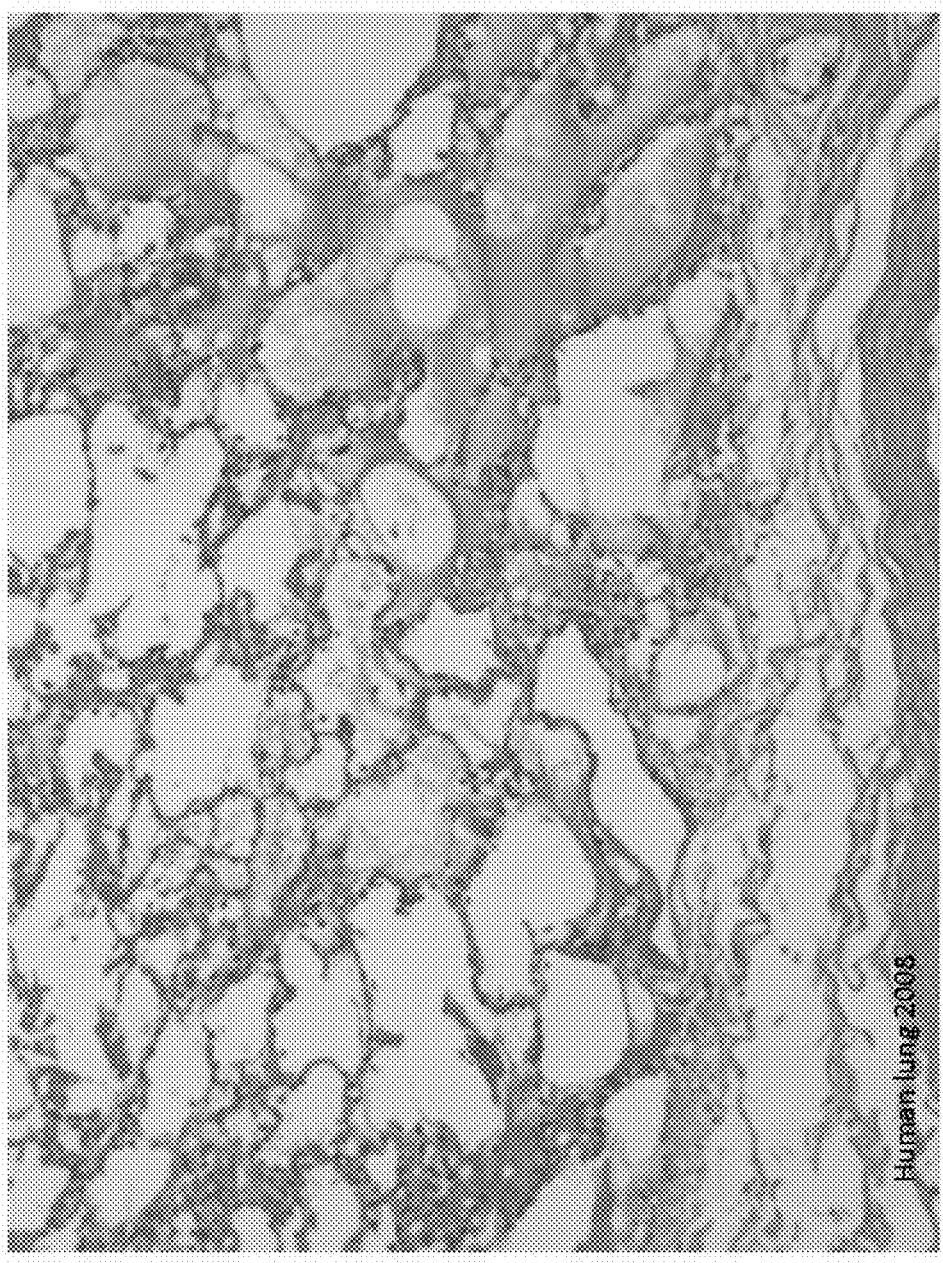
FIG. 5 is a human lung section prepared according to the method described in Example 2.
Figure 6:
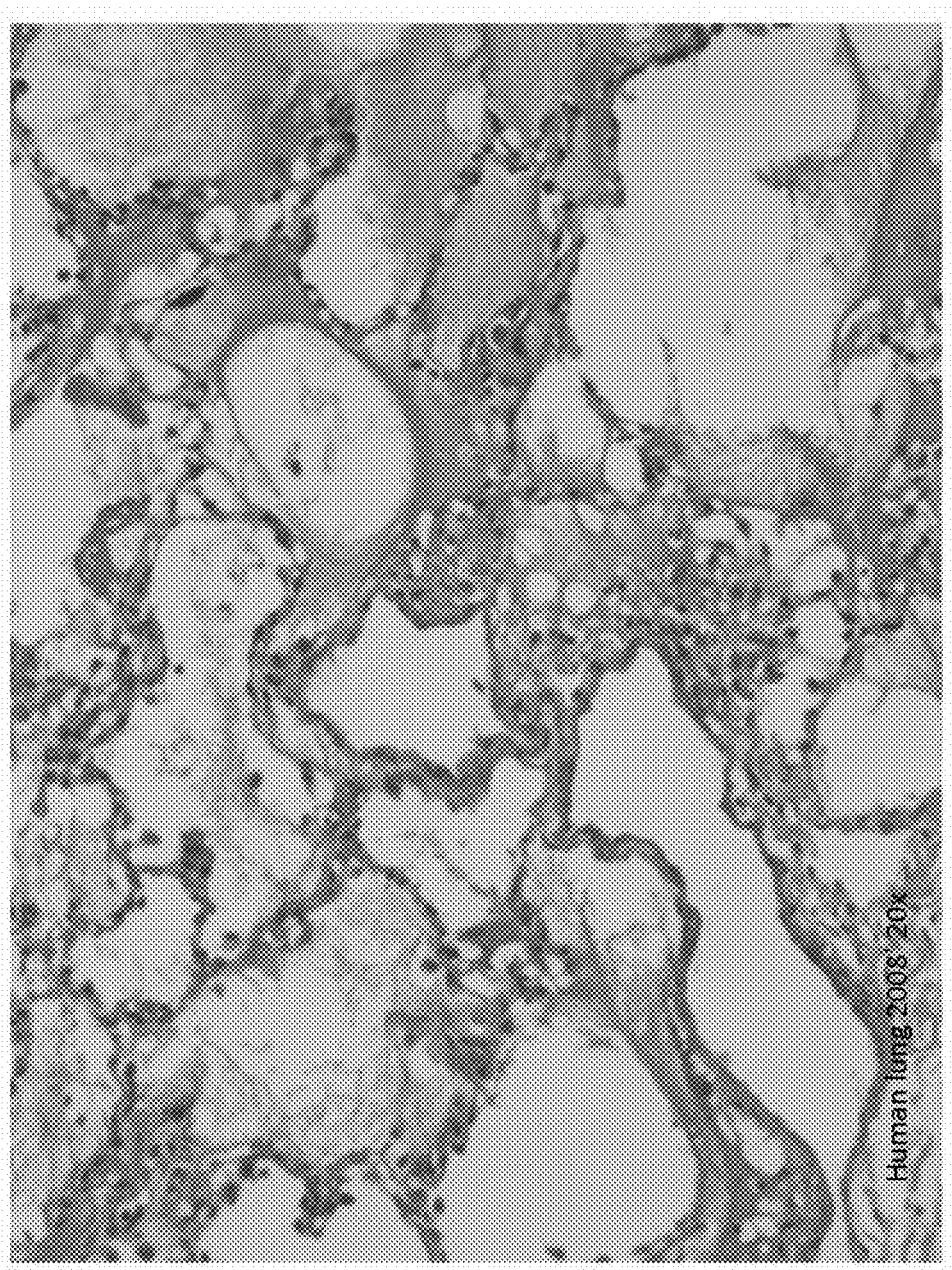
FIG. 6 is the human lung section of FIG. 5, magnified 20×.
Figure 7:
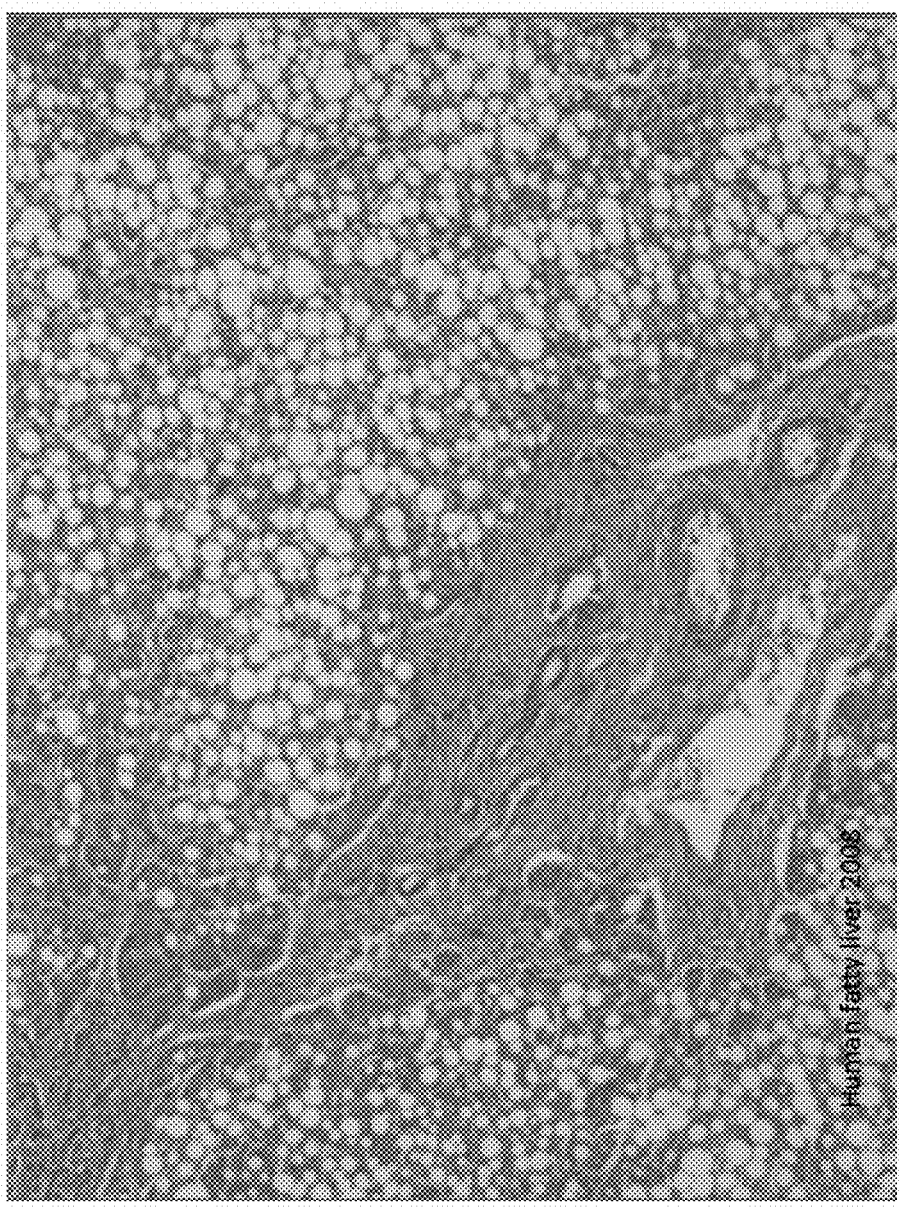
FIG. 7 is a human fatty liver section prepared according to the method described in Example 2.
Figure 8:
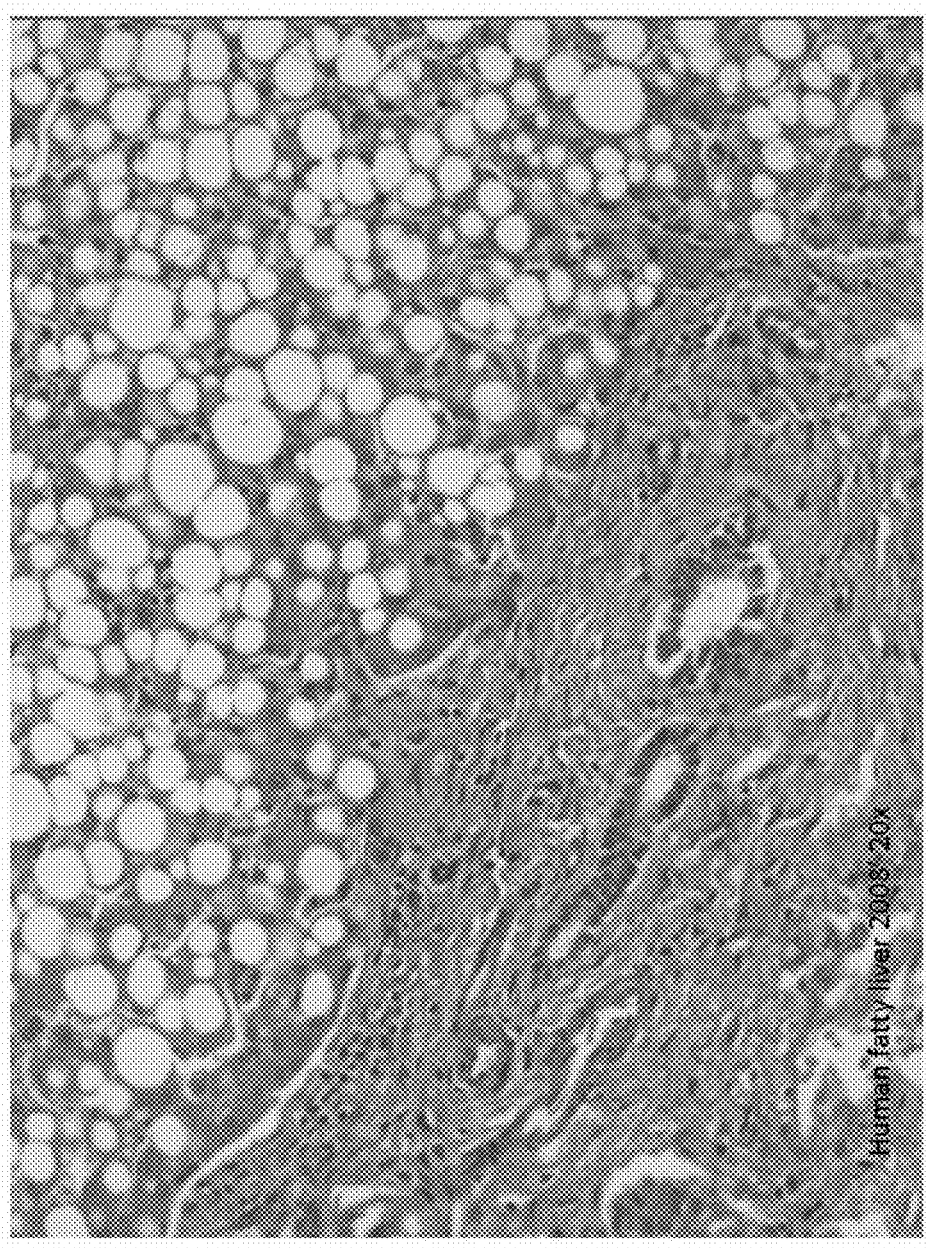
FIG. 8 is the human fatty liver section of FIG. 7, magnified 20×.
Figure 9:
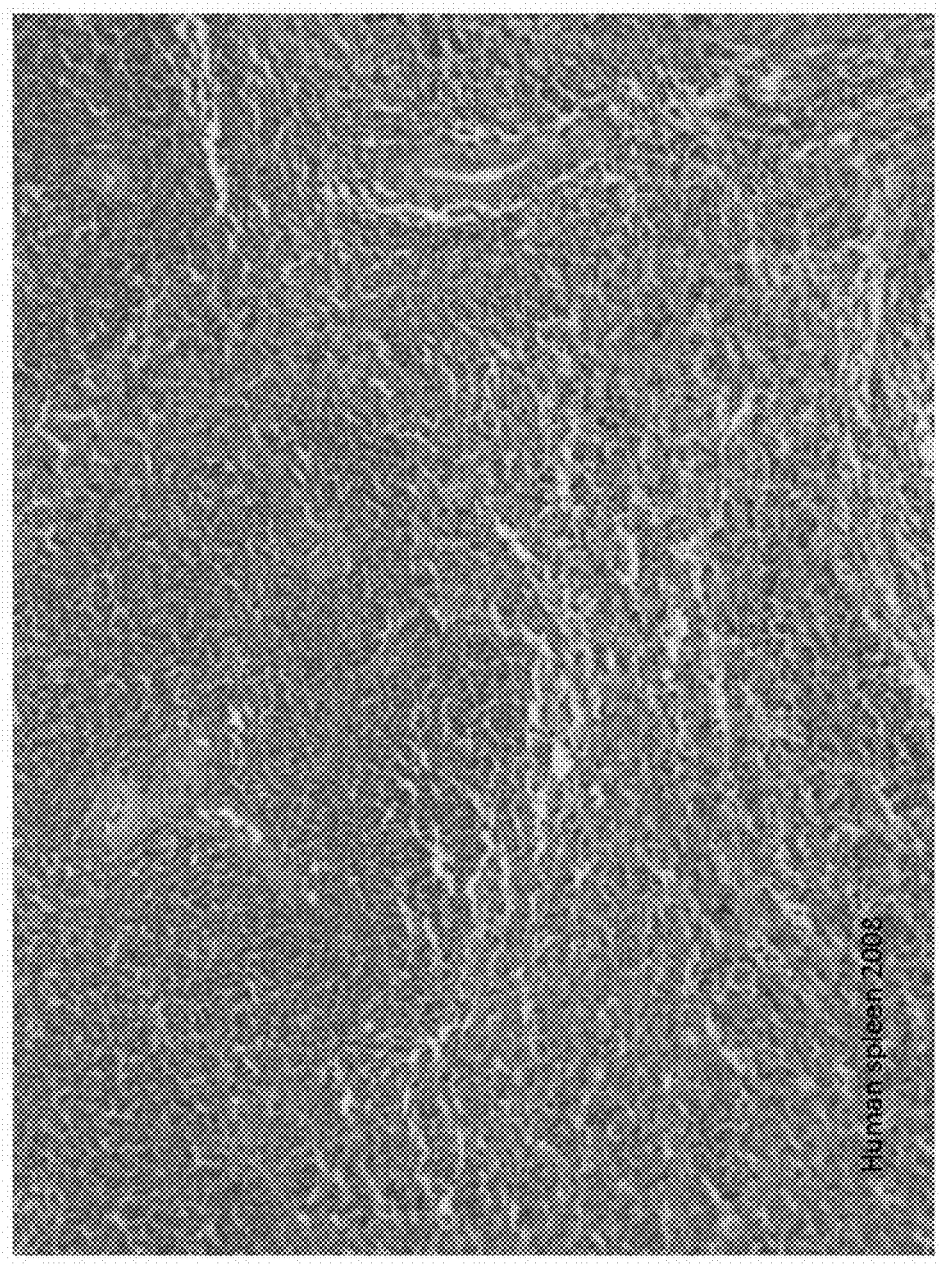
FIG. 9 is a human spleen section prepared according to the described in Example 2.
Figure 10:
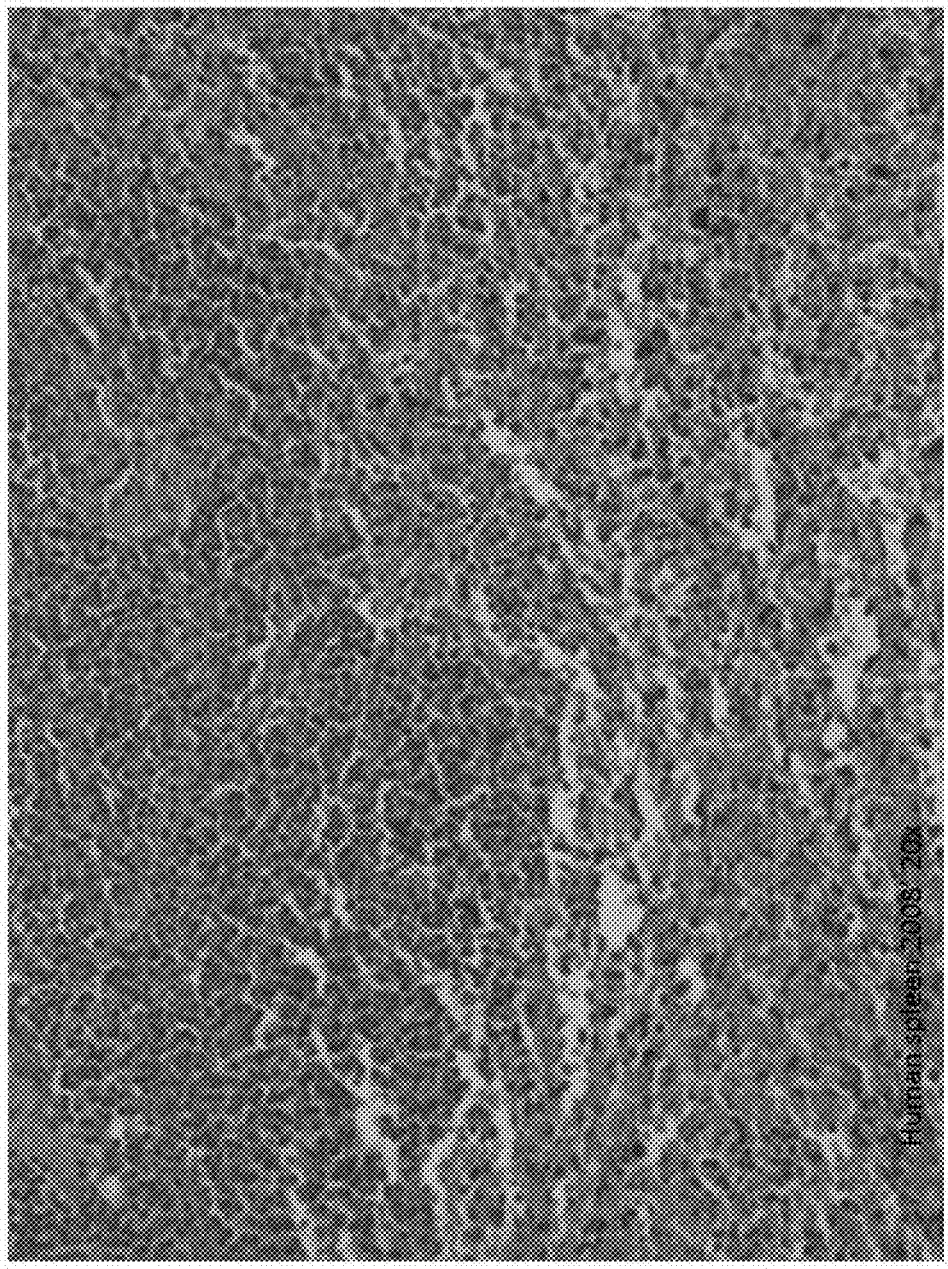
FIG. 10 is the human spleen liver section of FIG. 9, magnified 20×.
Figure 11:
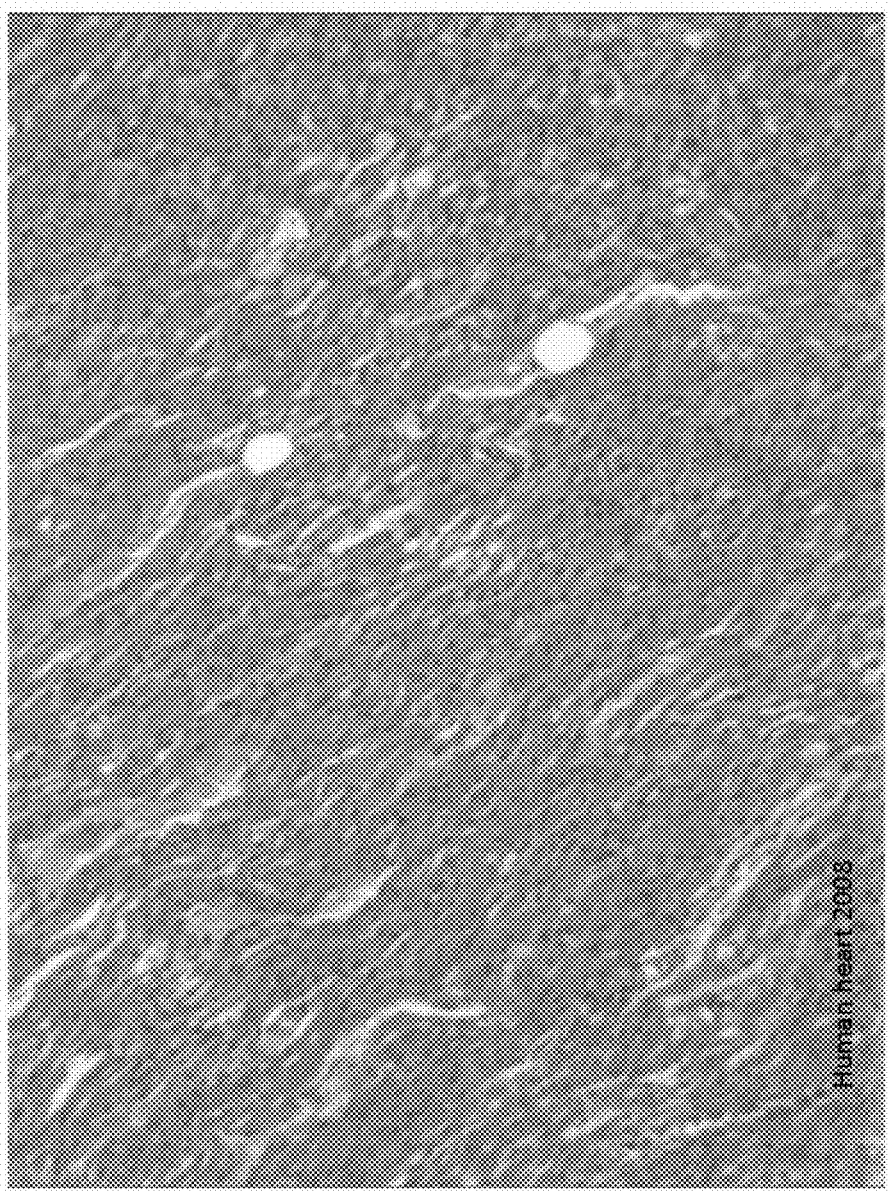
FIG. 11 is a human heart section prepared according to the method described in Example 2.
Figure 12:
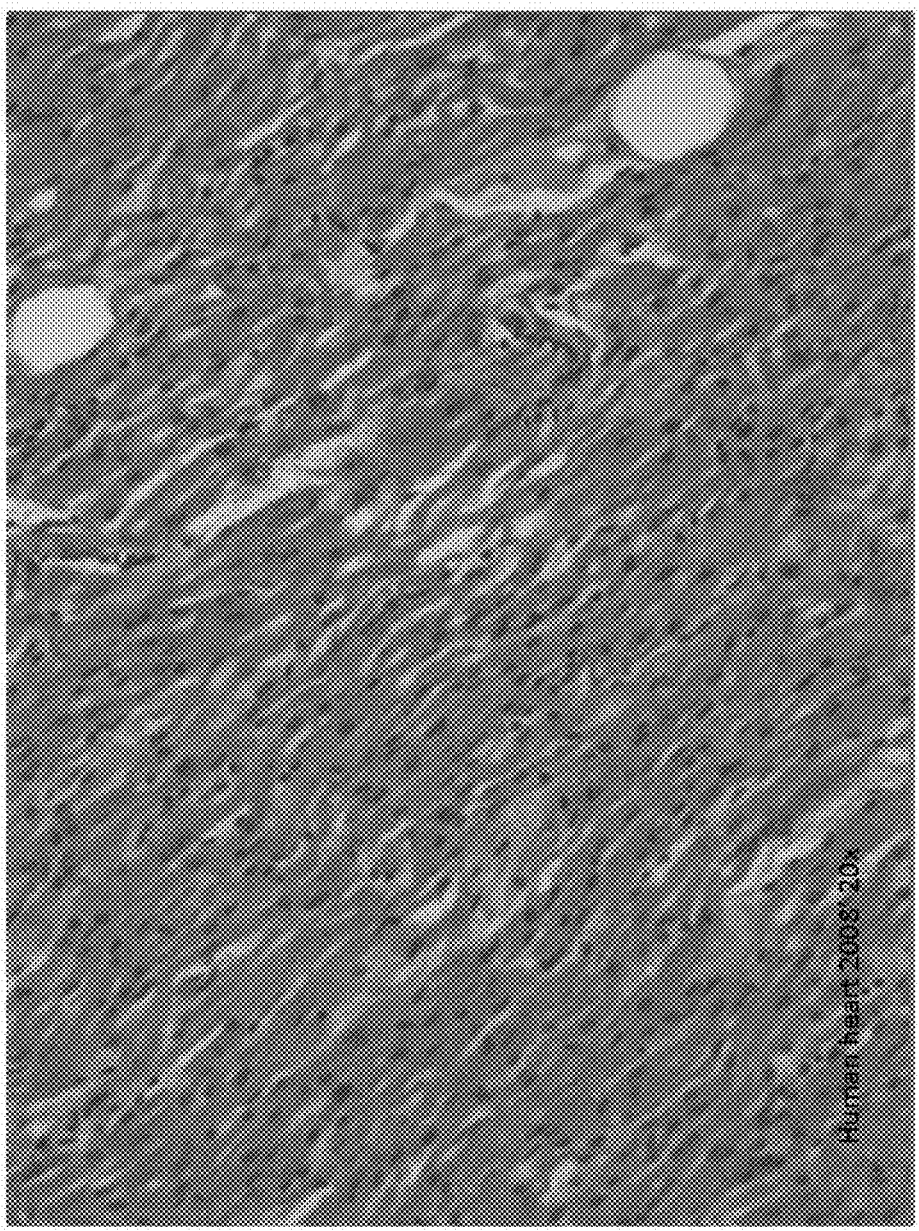
FIG. 12 is the human heart section of FIG. 11, magnified 20×.
Figure 21:
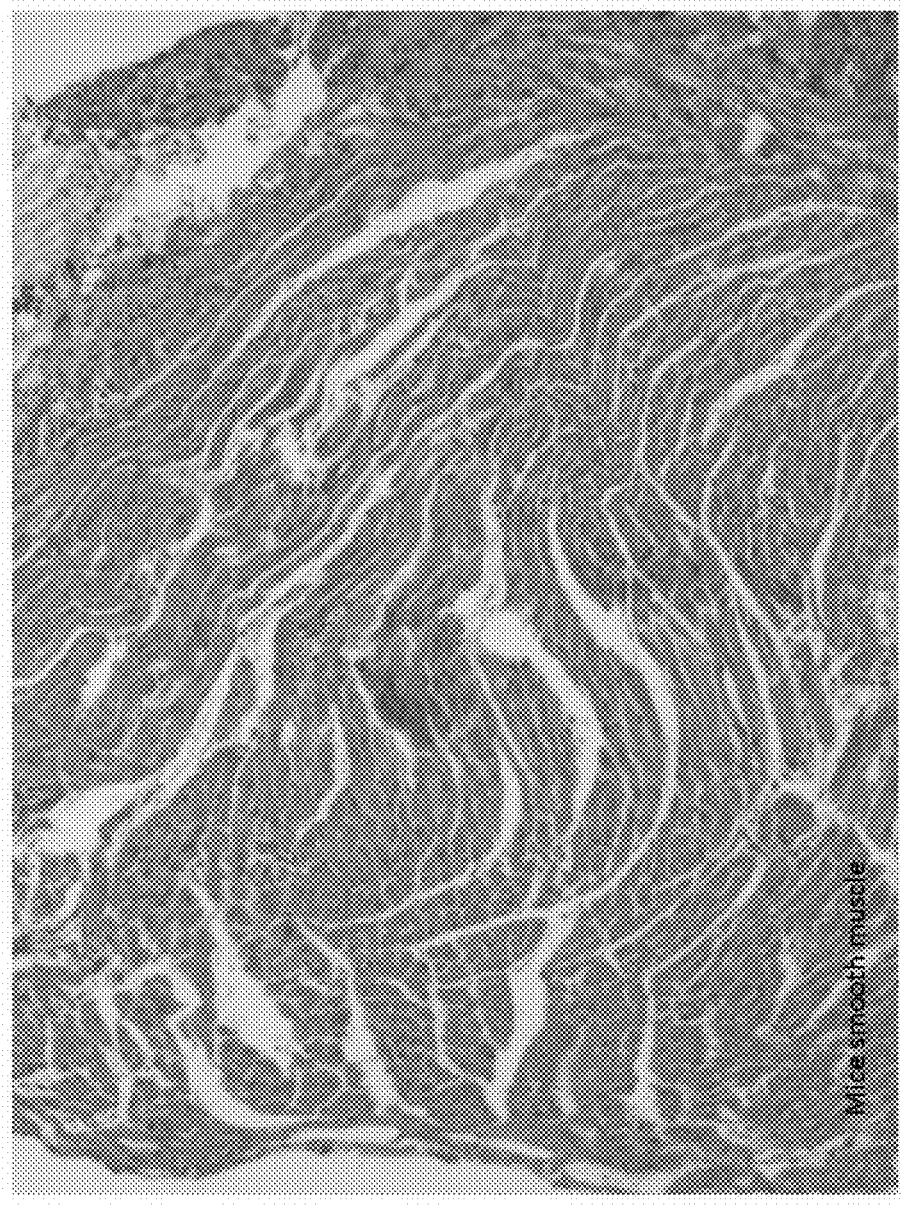
FIG. 21 is a mouse smooth muscle section prepared according to the method described in Example 2.
Figure 22:
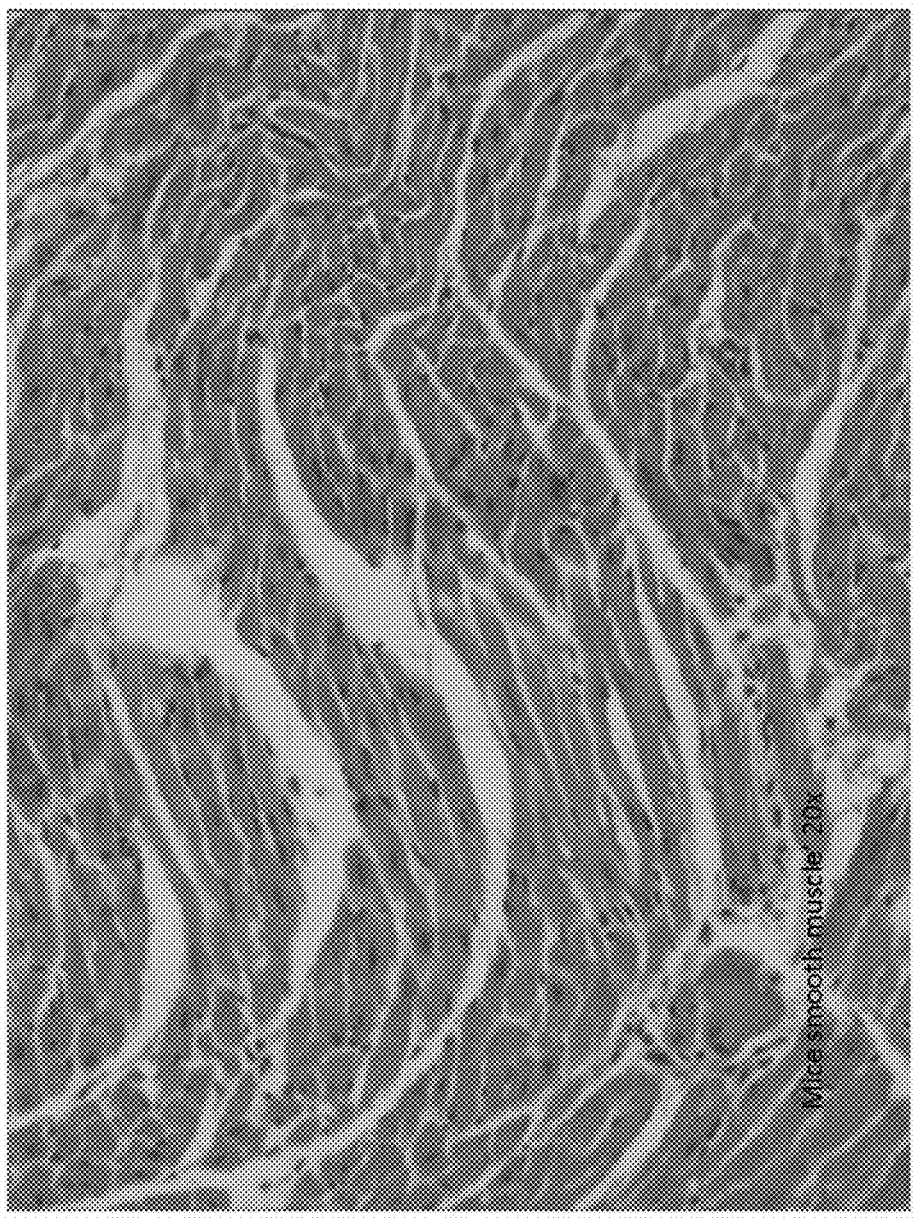
FIG. 22 is the mouse smooth muscle section of FIG. 21, magnified 20×.
Figure 23:
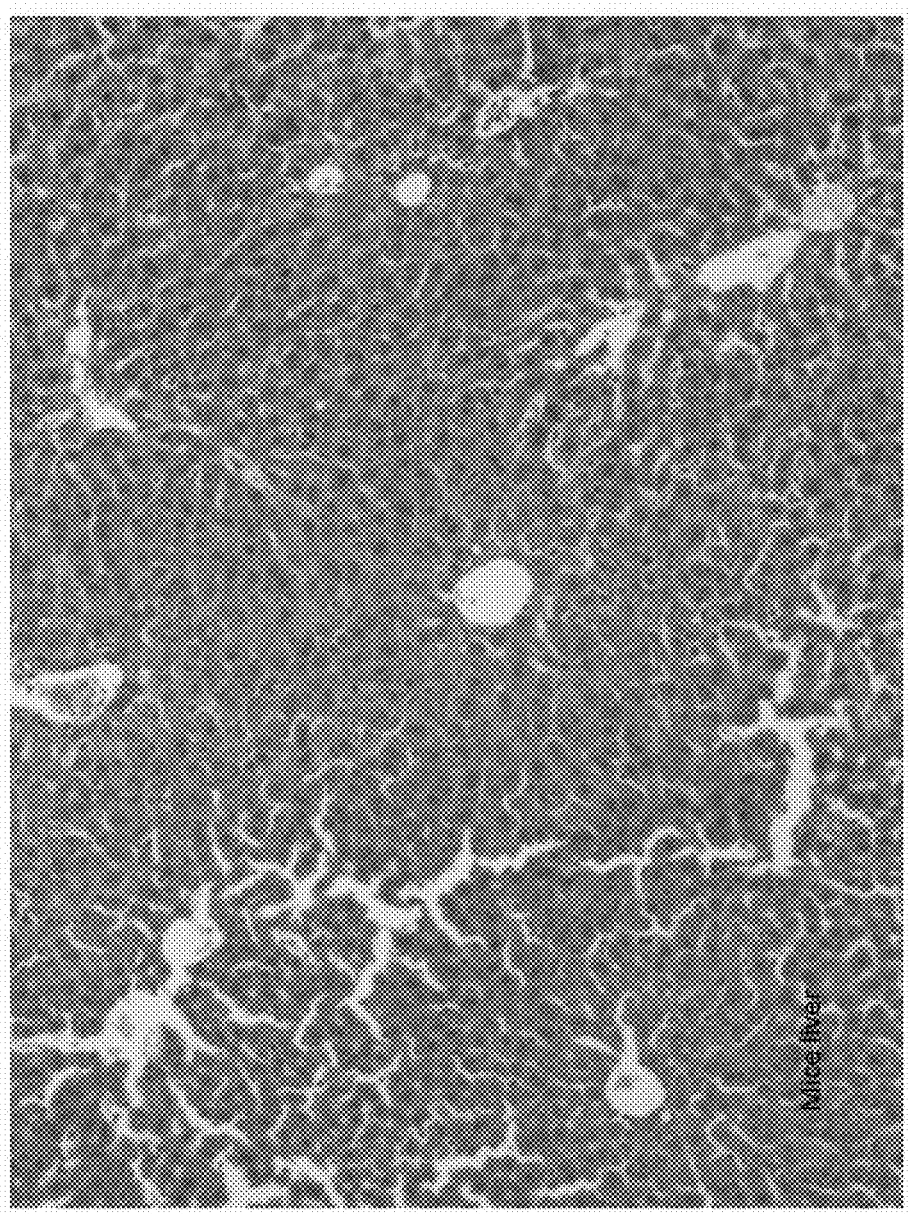
FIG. 23 is a mouse liver section prepared according to the method as described in Example 2.
Figure 24:
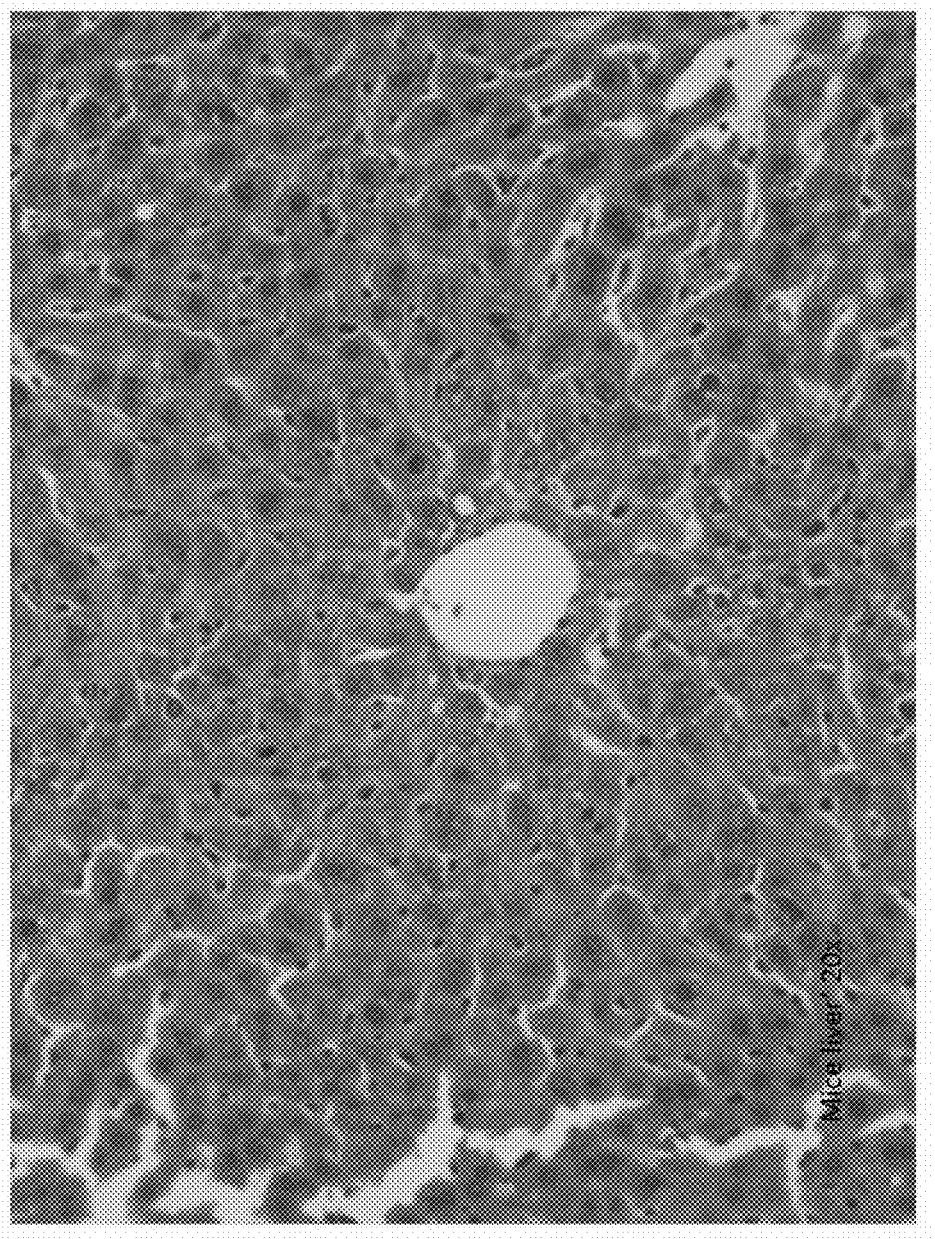
FIG. 24 is the mouse liver section of FIG. 21, magnified 20×.
Figure 25:
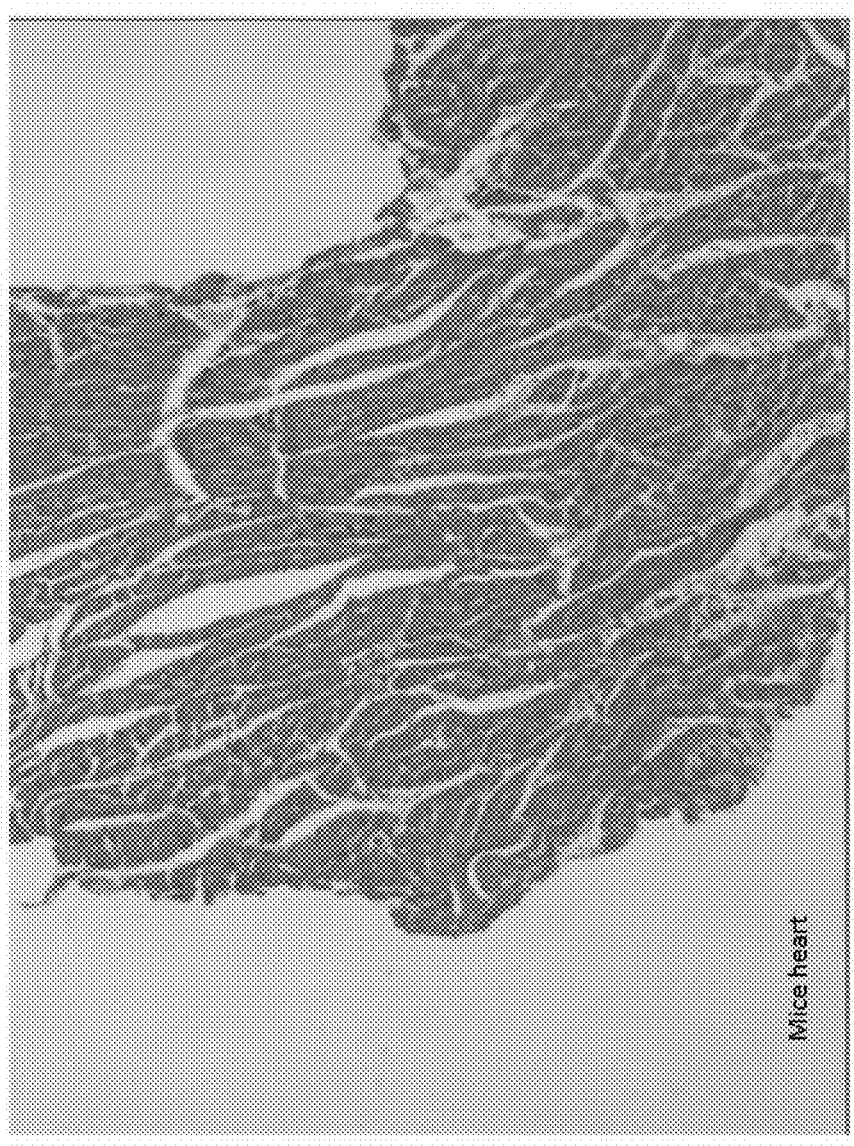
FIG. 25 is a mouse heart section prepared according to the method as described in Example 2.
Figure 26:
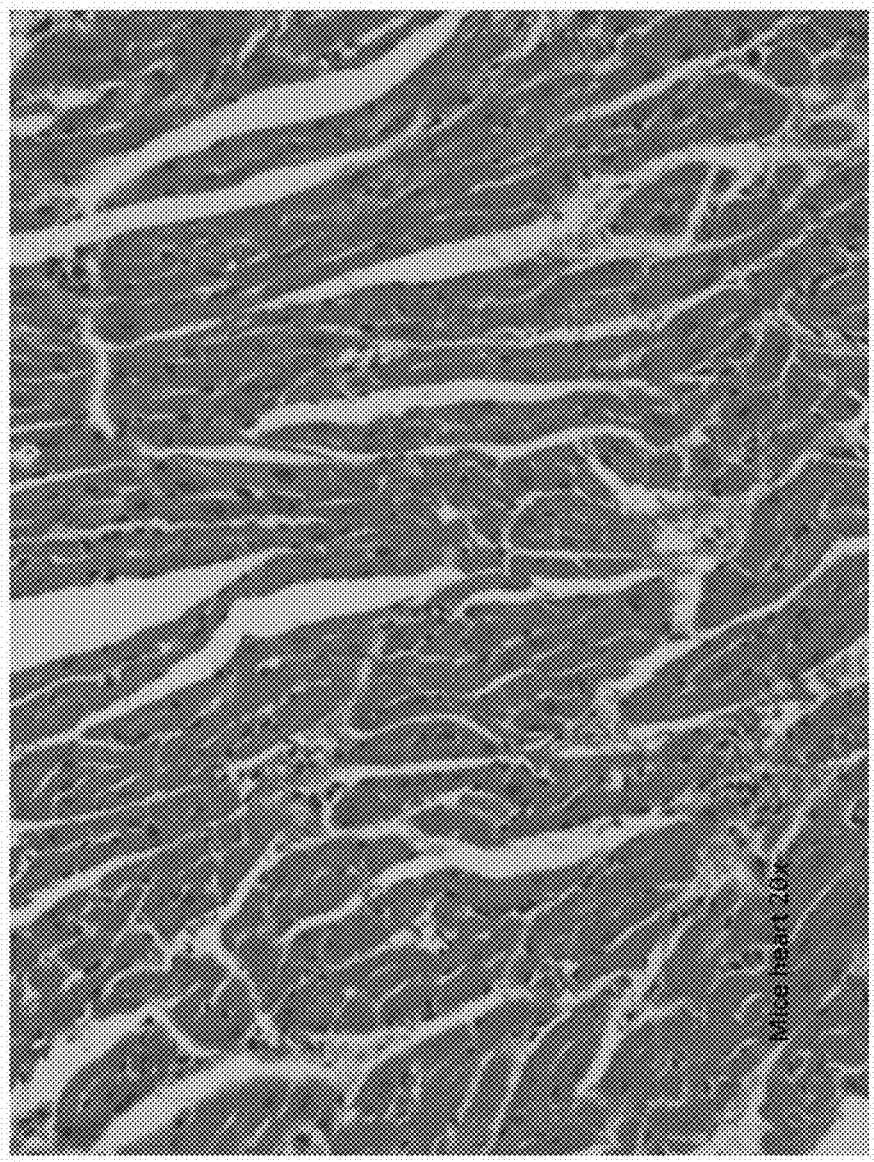
FIG. 26 is the mouse heart section of FIG. 25, magnified 20×.
Figure 27:
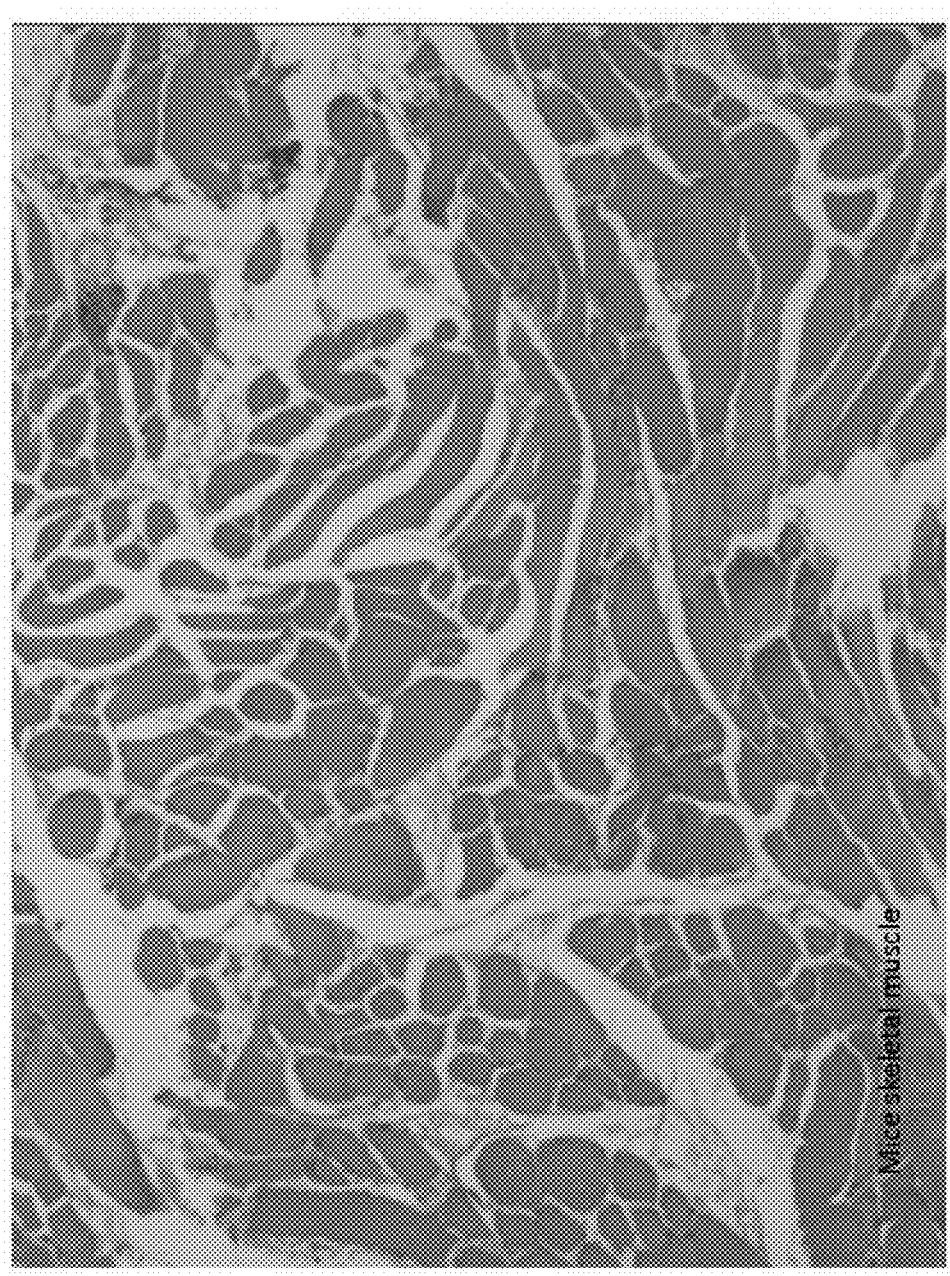
FIG. 27 is a mouse skeletal muscle section prepared according to the method described in Example 2.
Figure 28:
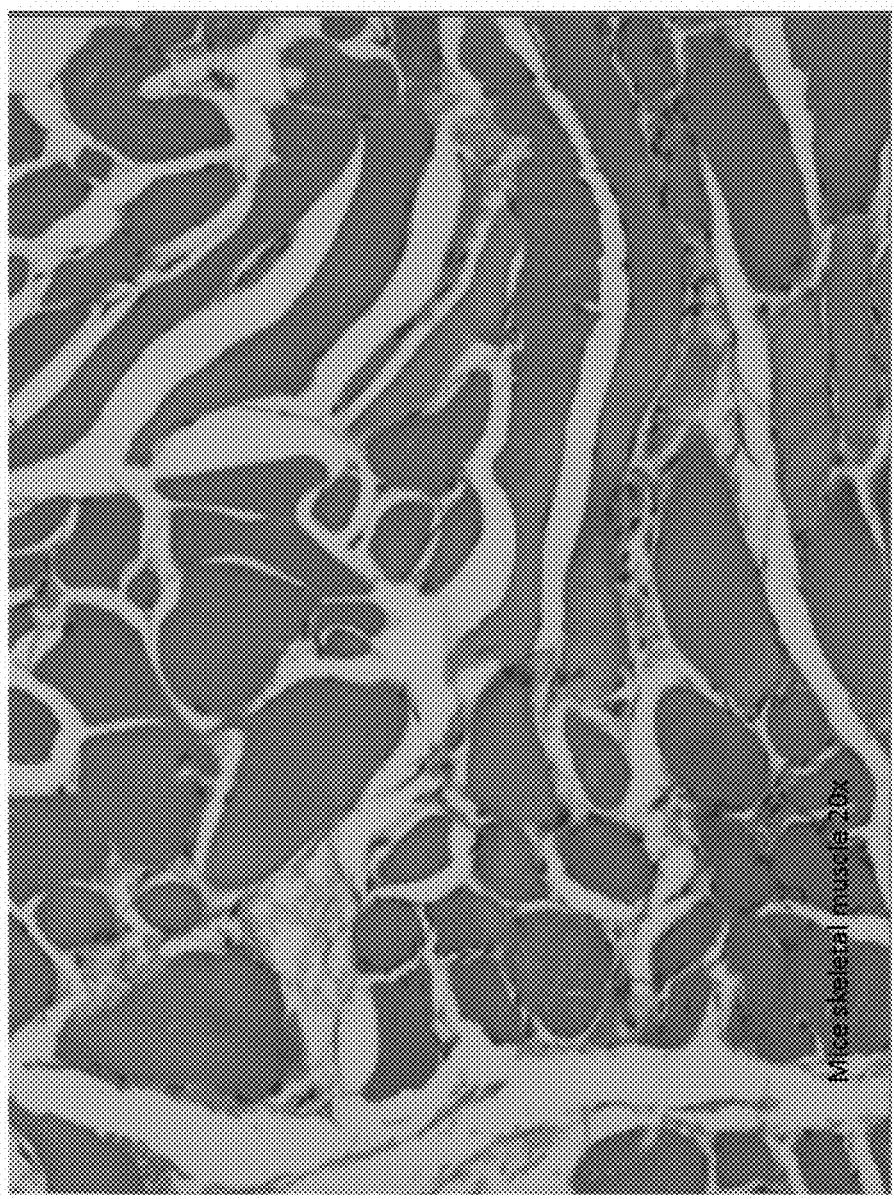
FIG. 28 is the mouse skeletal muscle section of FIG. 27, magnified 20×.
Figure 29:
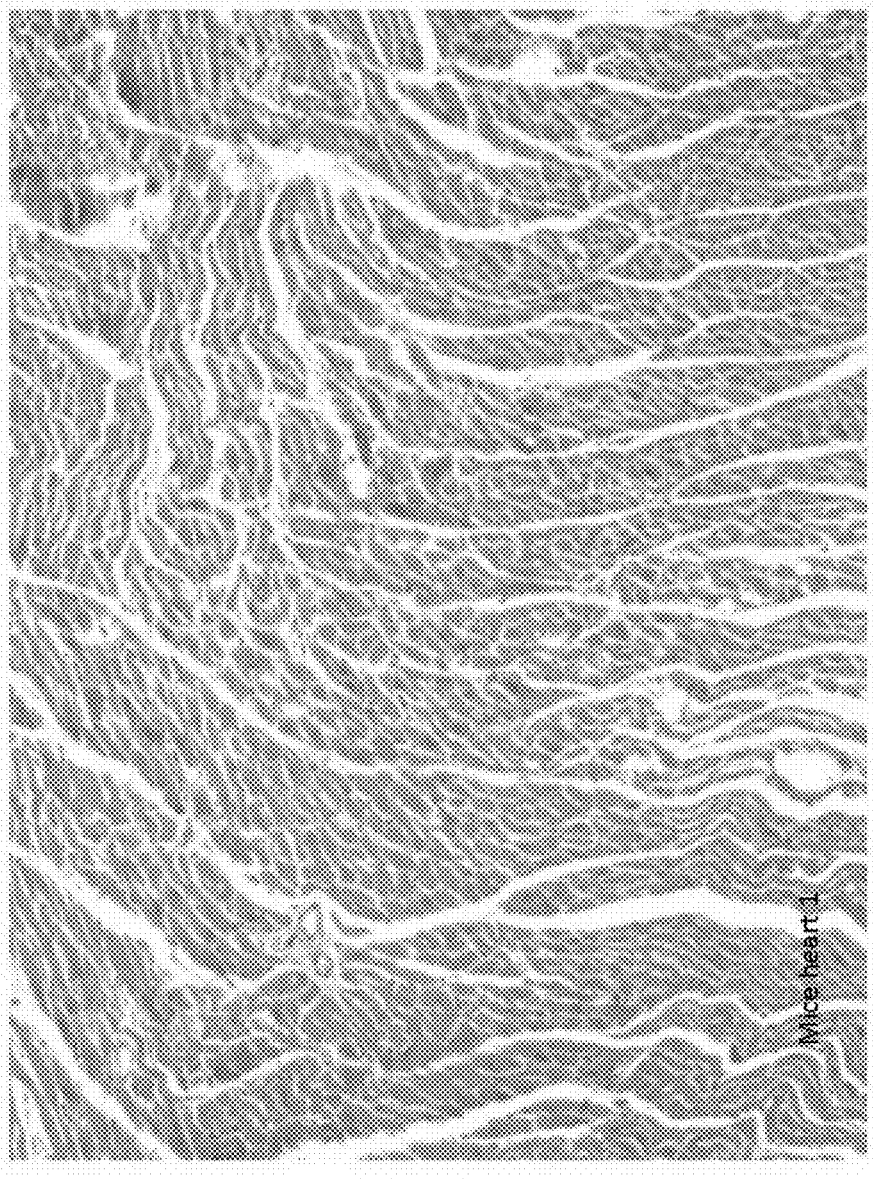
FIG. 29 is a mouse heart section prepared according to the method described in Example 2.
Figure 30:
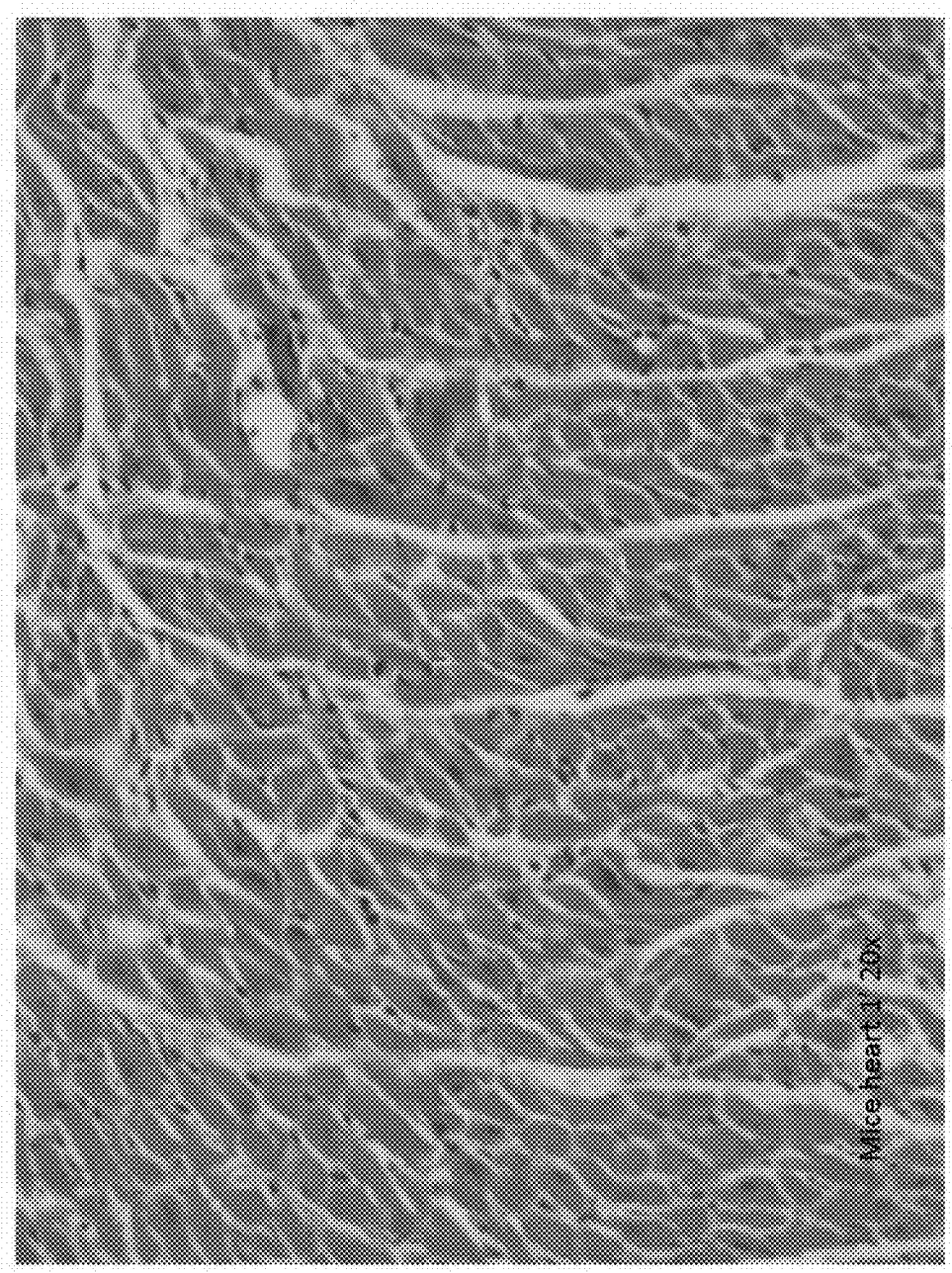
FIG. 30 is the mouse heart section of FIG. 29, magnified 20×.
Figure 31:
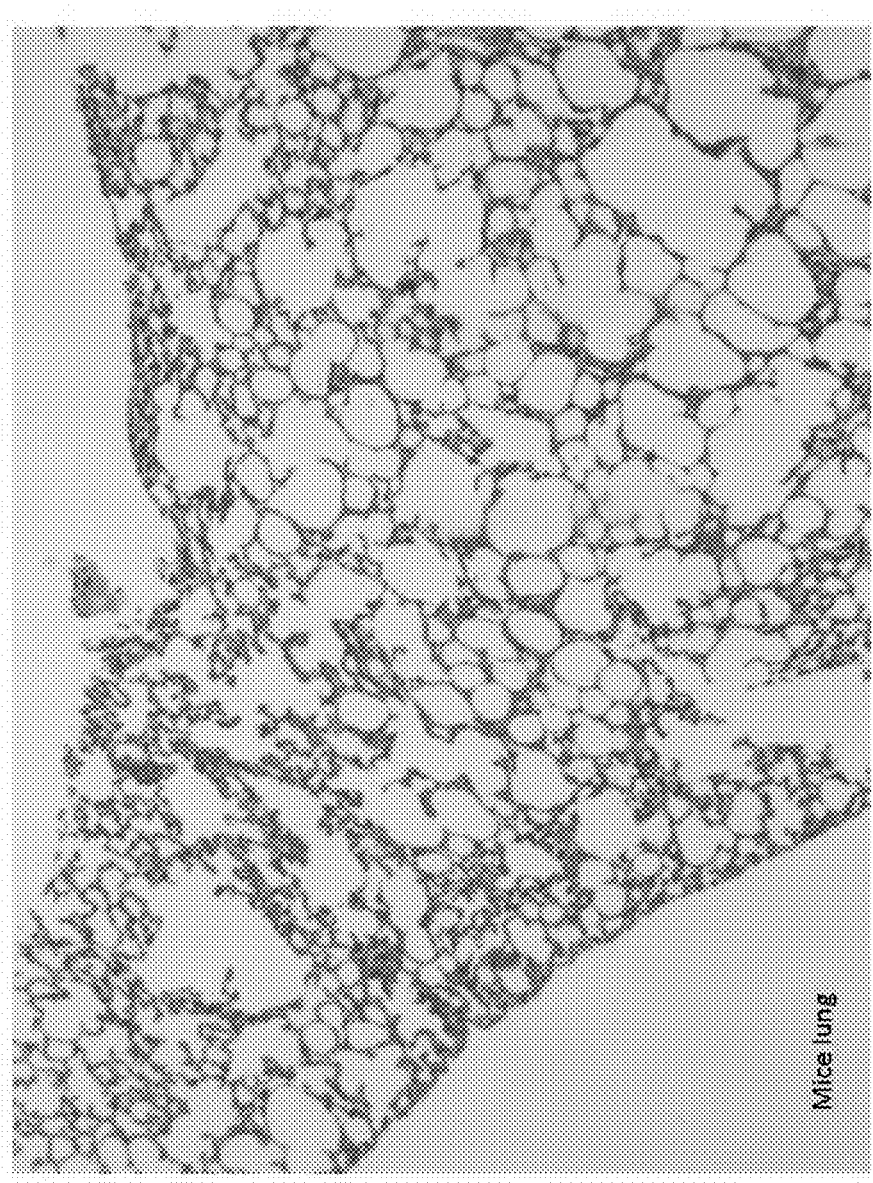
FIG. 31 is a mouse lung section prepared according to the method described in Example 2.
Figure 32:
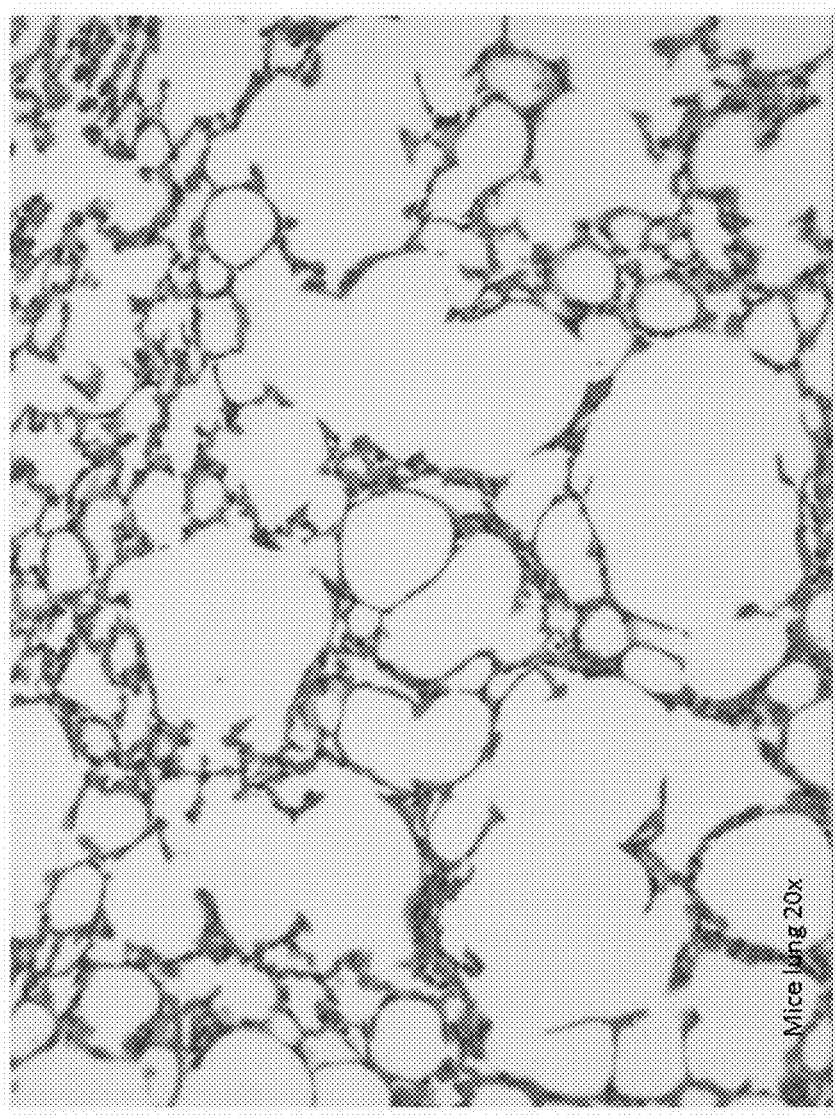
FIG. 32 is the mouse lung section of FIG. 31, magnified 20×.
Figure 33:
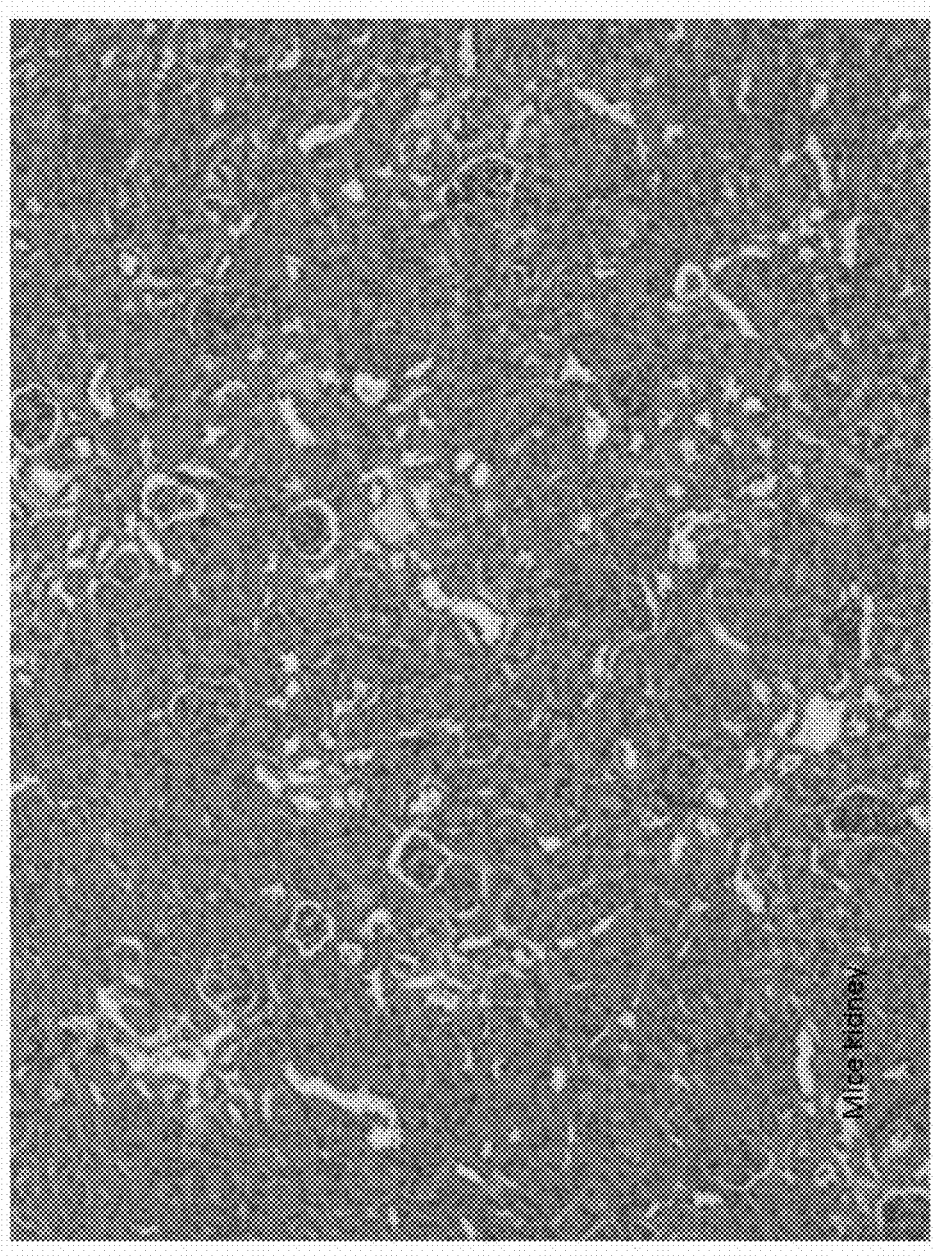
FIG. 33 is a mouse kidney section prepared according to the method described in Example 2.
Figure 34:
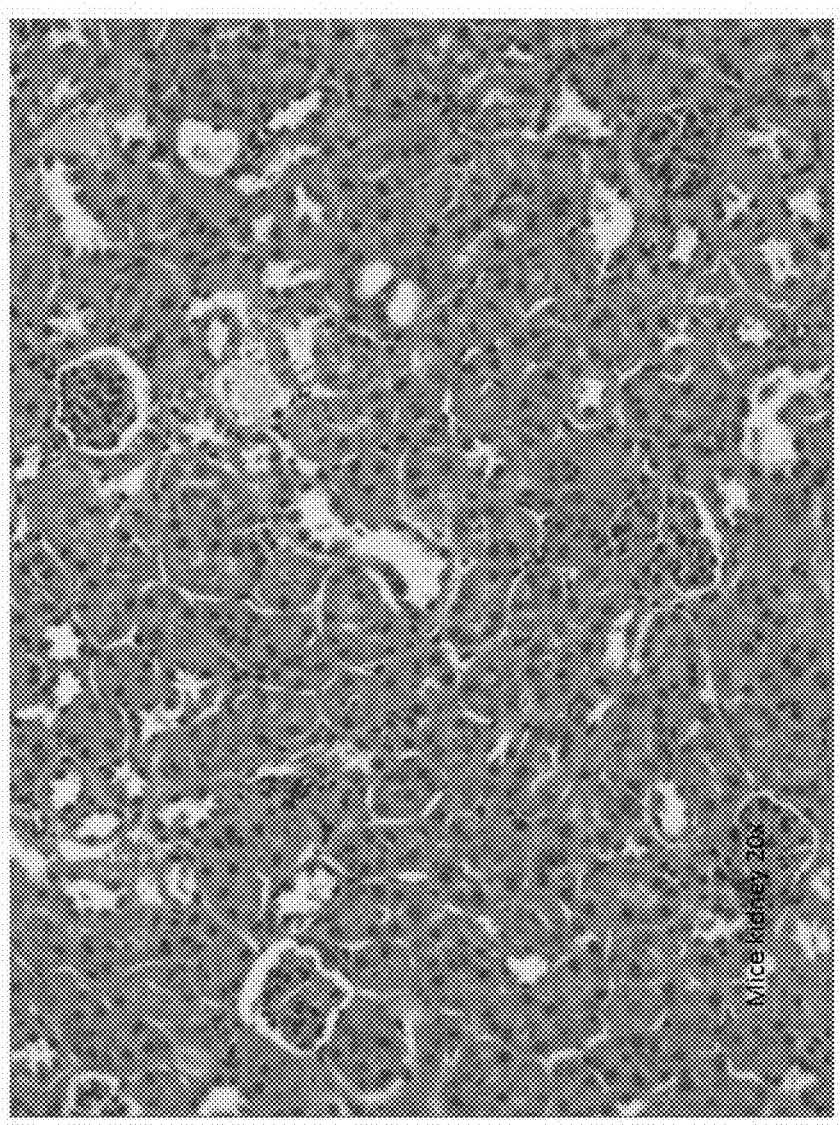
FIG. 34 is the mouse kidney section of FIG. 33, magnified 20×.
Figure 35:
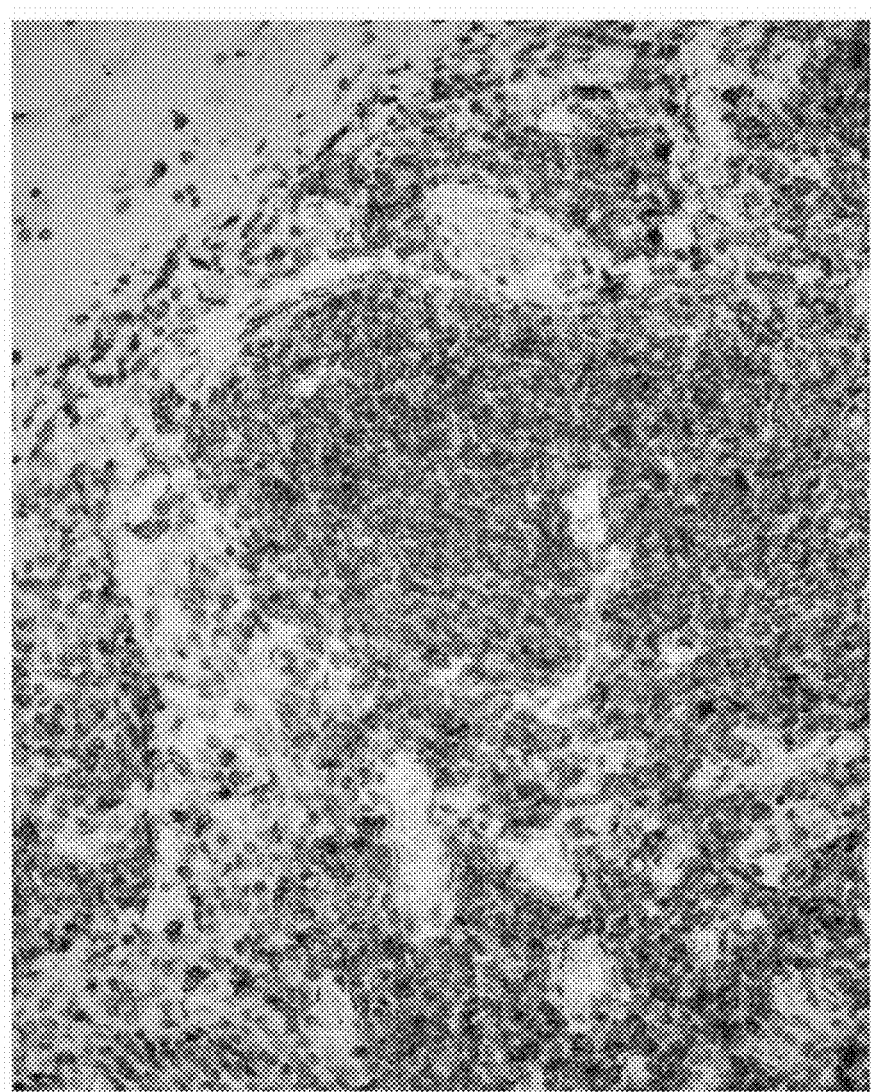
FIG. 35 is a human colon section prepared according to the method described in Example 2, stained for cytokeratin.
Figure 37:
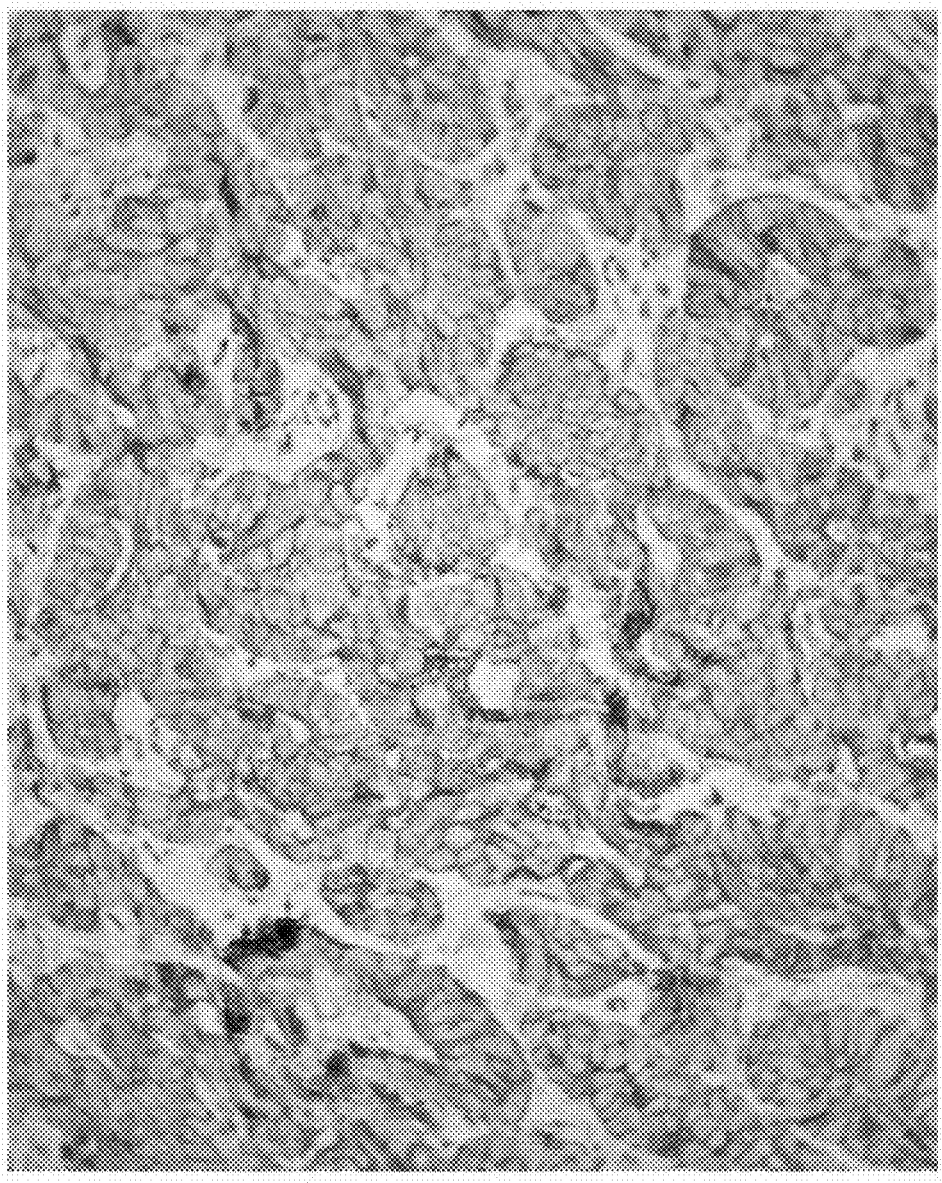
FIG. 37 is a human lymphoma section prepared according to the method described in Example 2, stained for human leukocyte antigen.

Samples were coverslipped and viewed under a microscope. Slides were found to be comparable to slides prepared according to commonly used procedures. Slides showing the 4 µm sections prepared according to this method can be seen in FIGS. 5-12, 21-35 and 37.

Example 3

Control Slides

Briefly, all samples are biopsied and placed into containers containing 10% formalin. Upon receipt by the lab (up to 18 hours later), the samples were subject to the following procedure, which is carried out at 37° C.

Formalin 10%-10 hours
Alcohol (ethanol), 70%—30 minutes
Alcohol (ethanol), 95%—45 minutes
Alcohol (ethanol), 95%—45 minutes
Alcohol (ethanol), 100%—1 hour
Alcohol (ethanol), 100%—1 hour
Alcohol (ethanol), 100%—1 hour
Xylene—1 hour
Xylene—1 hour The sample was then infiltrated with paraffin (2 changes) for 45 min each. This was performed at about 60° C. The samples were then embedded in paraffin according to standard protocols. The samples were sectioned on a microtome to a thickness of 4 µM.

The section was then de-paraffinized according to standard procedures. In brief: the sample was immersed for 2 minutes in histology grade xylene. This was performed 4 times. Now that the paraffin is removed, the excess xylene is removed. The sample is immersed for 1 minute in absolute ethanol (2×). The sample is immersed for 30 seconds in 95% ethanol. The sample is immersed for 45 seconds in 70% ethanol. The sample is washed with water for 1 minute. The slides were stained according to standard procedures.

Figure 2:
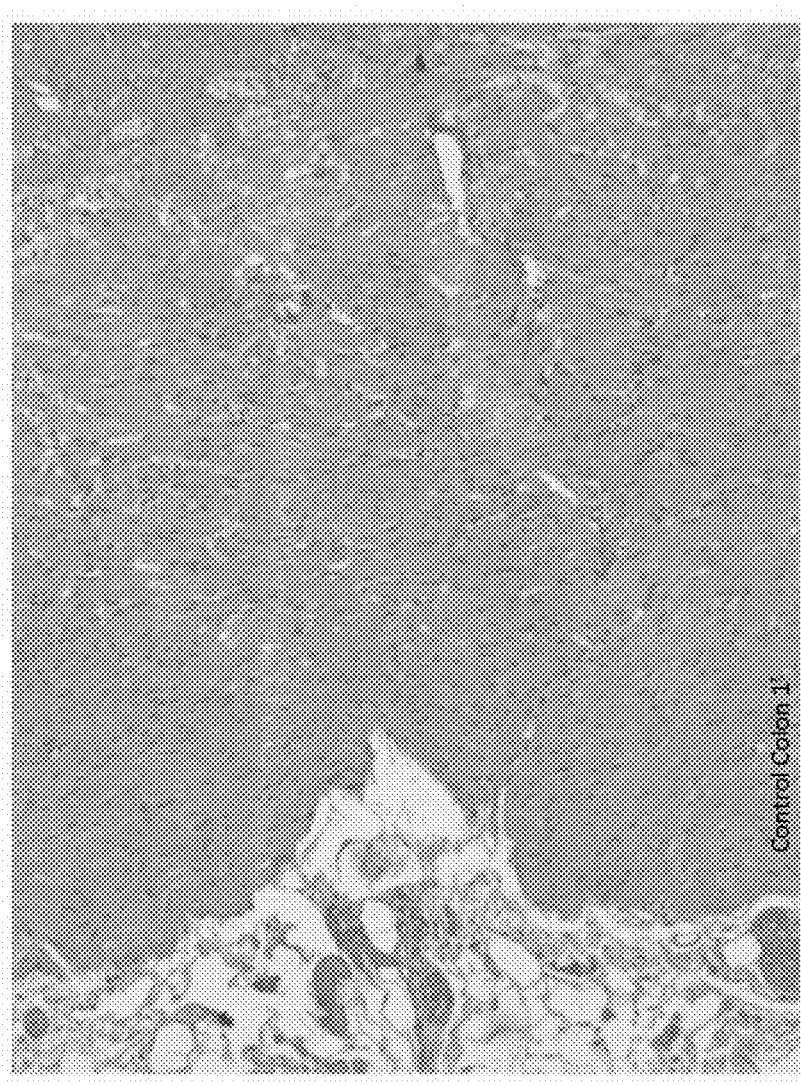
FIG. 2 is a different control human colon section prepared according to the method described in Example 3.
Figure 3:
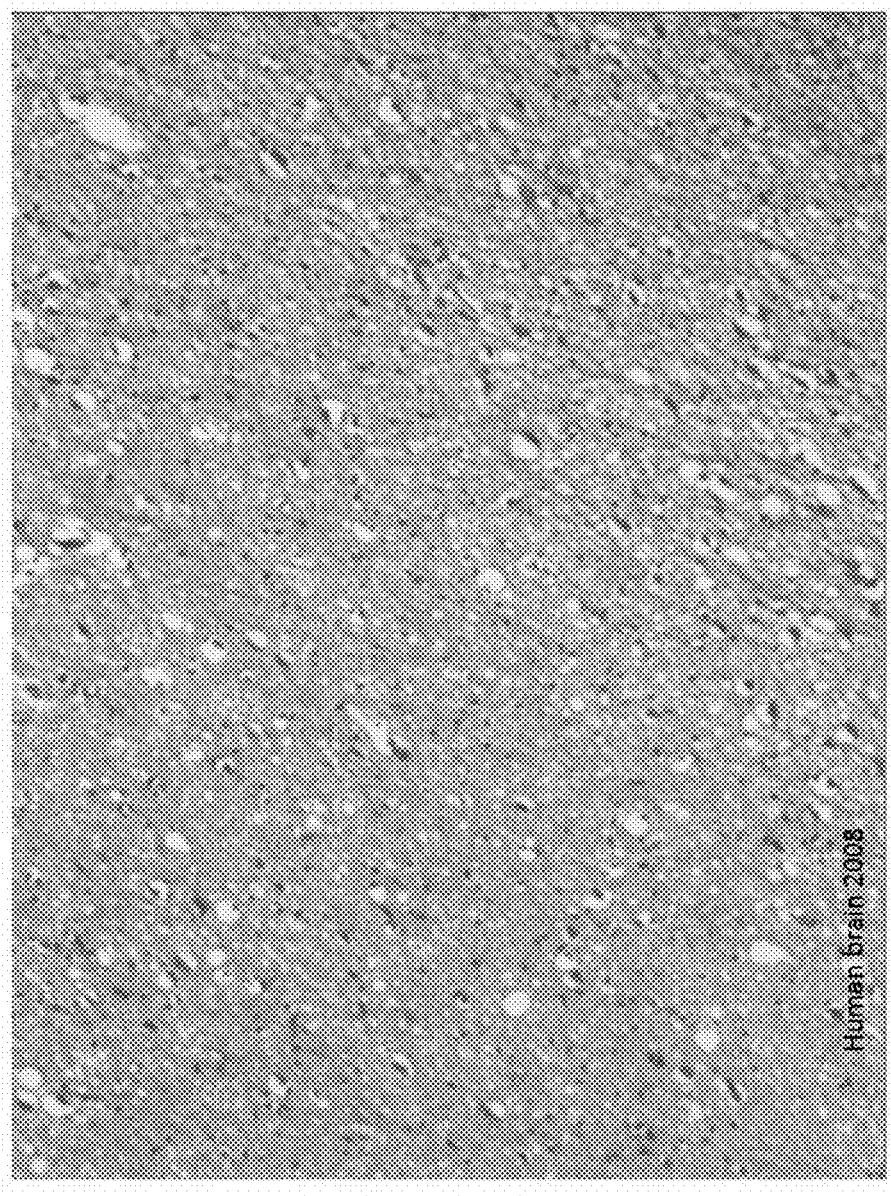
FIG. 3 is a human colon section prepared according to the method described in Example 2.
Figure 4:
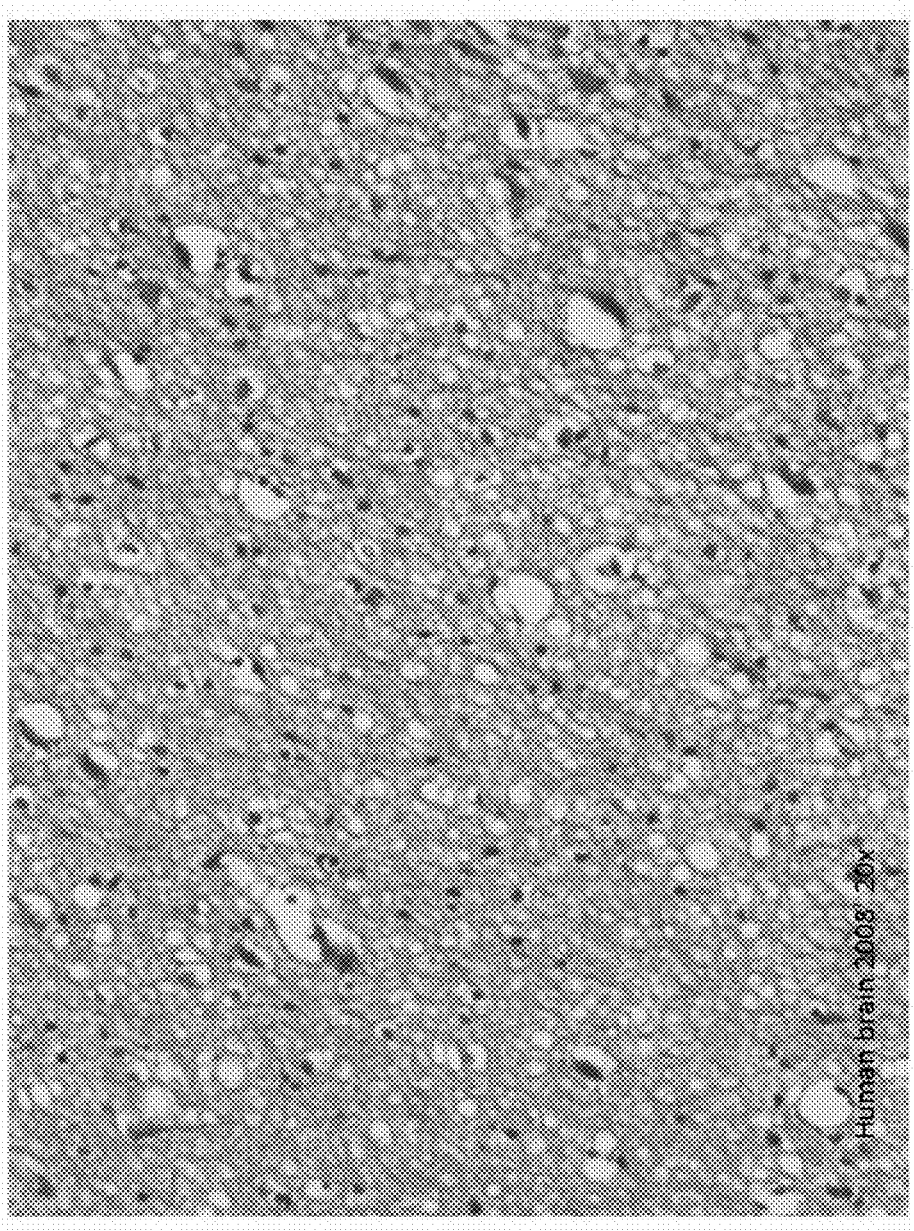
FIG. 4 is the human colon section of FIG. 3, magnified 20×.
Figure 13:
FIG. 13 is a control human colon section prepared according to the method described in Example 3.
Figure 14:
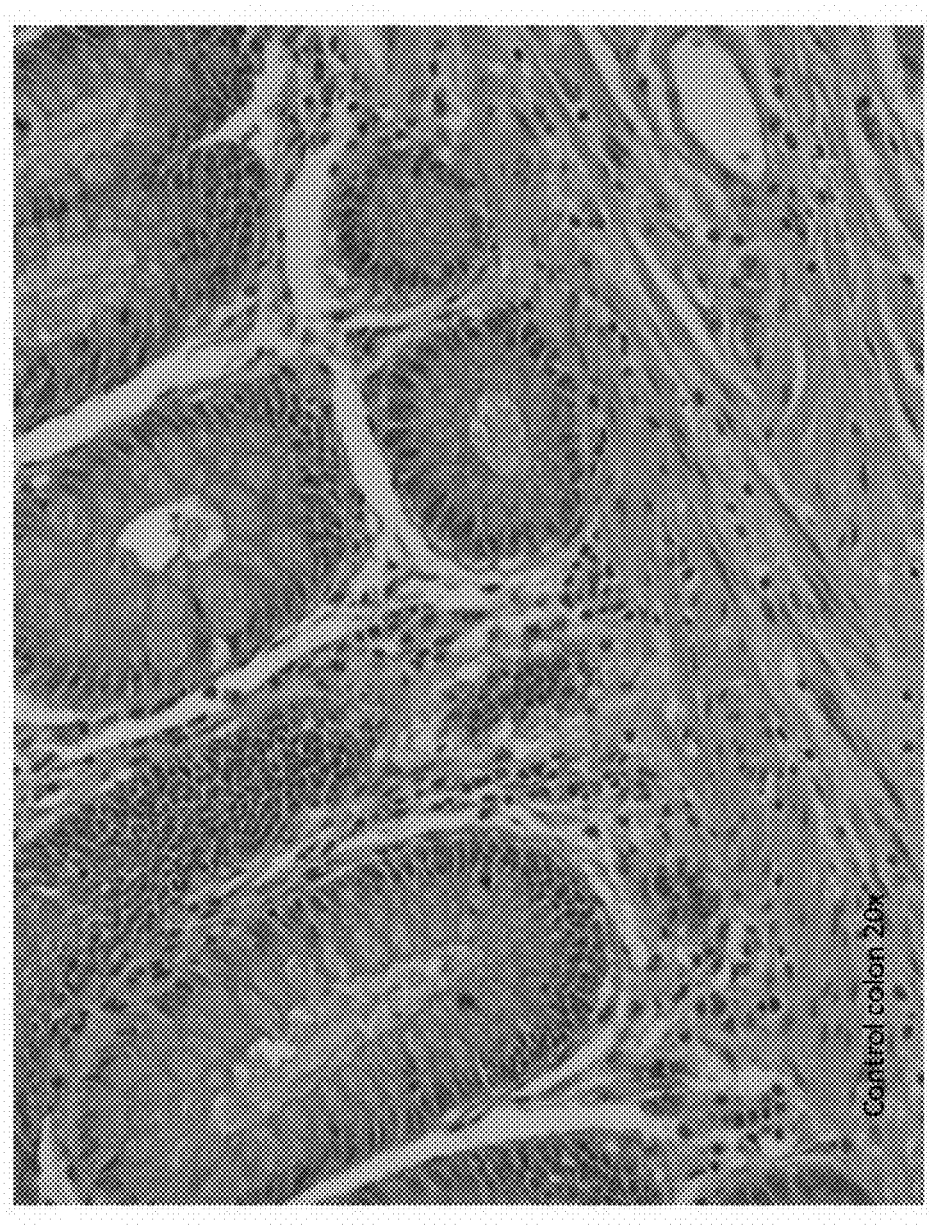
FIG. 14 is the control human colon section of FIG. 13, magnified 20×.
Figure 15:
FIG. 15 is a control human colon section prepared according to the method described in Example 3.
Figure 16:
FIG. 16 is the control human colon section of FIG. 15, magnified 20×.
Figure 17:
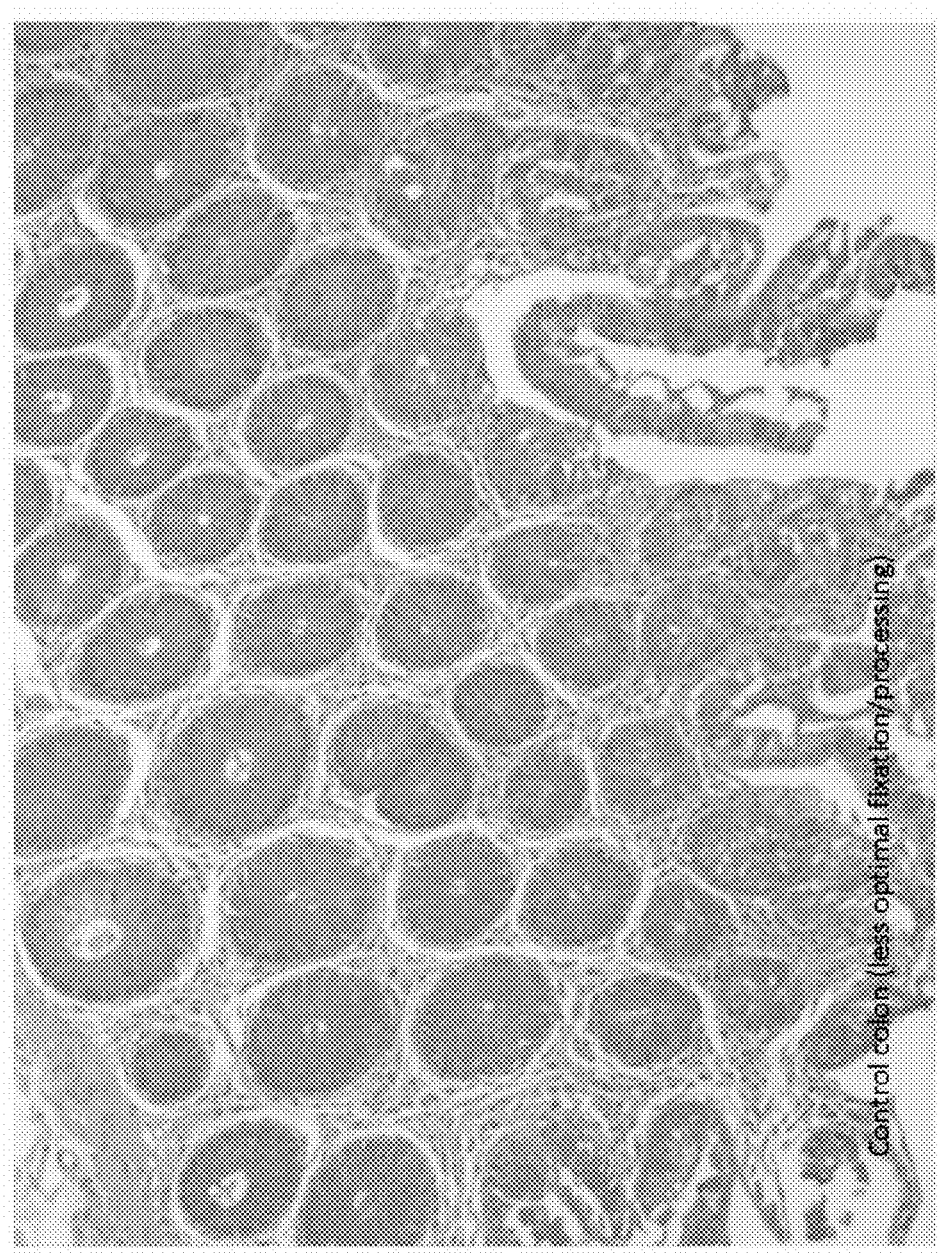
FIG. 17 is a control human colon section prepared according to a less optimal fixation/processing procedure of the prior art.
Figure 18:
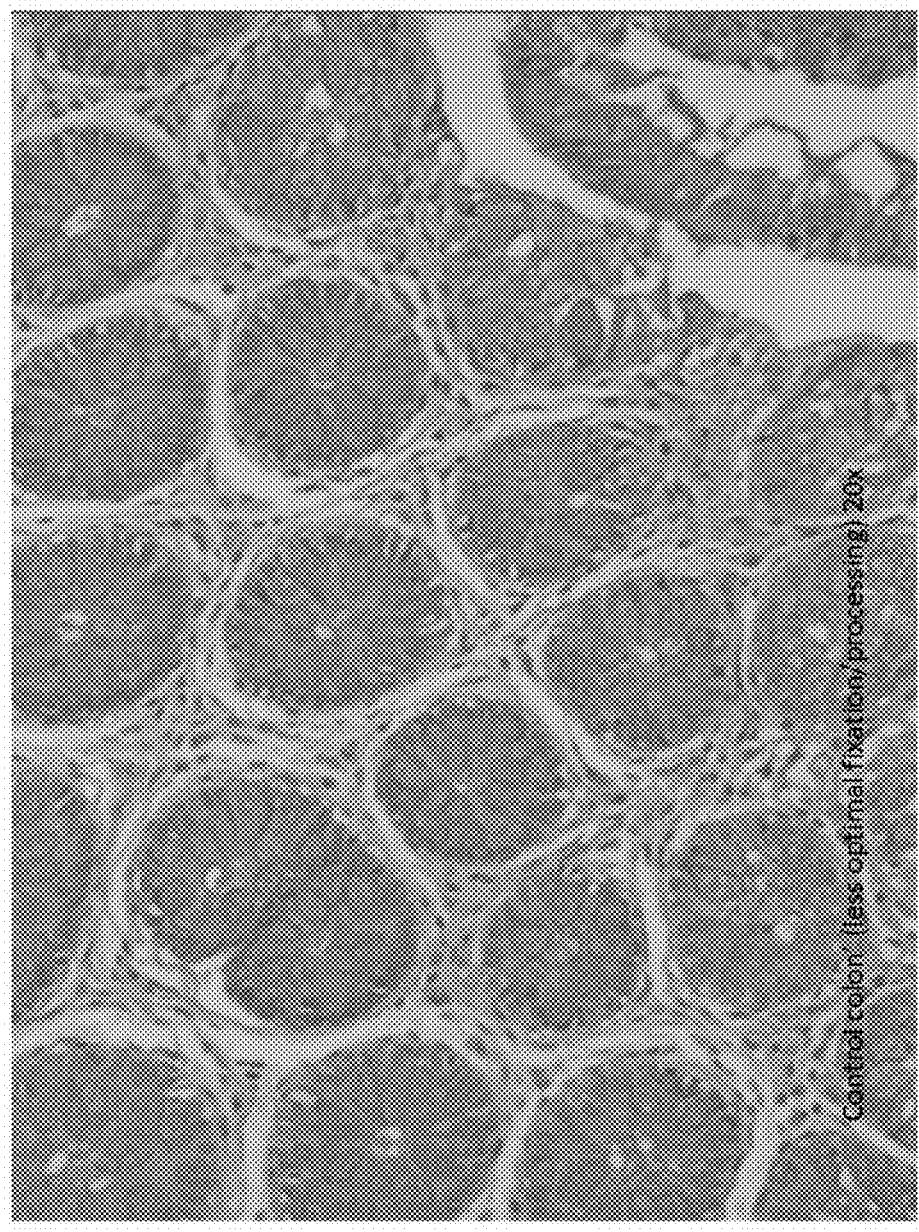
FIG. 18 is the control human colon section of FIG. 17, magnified 20×.
Figure 19:
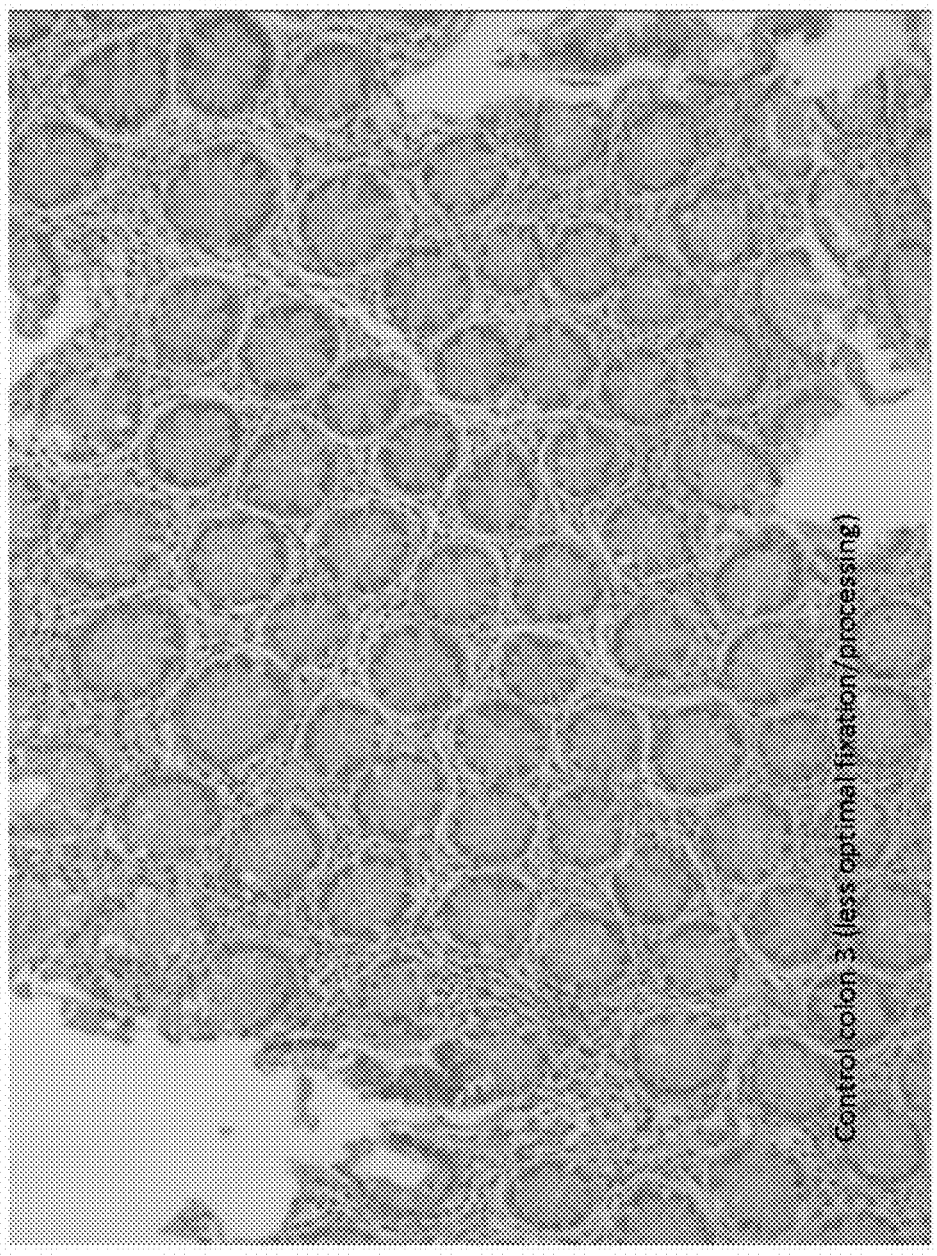
FIG. 19 is a control human colon section prepared according to a less optimal fixation/processing procedure of the prior art.
Figure 20:
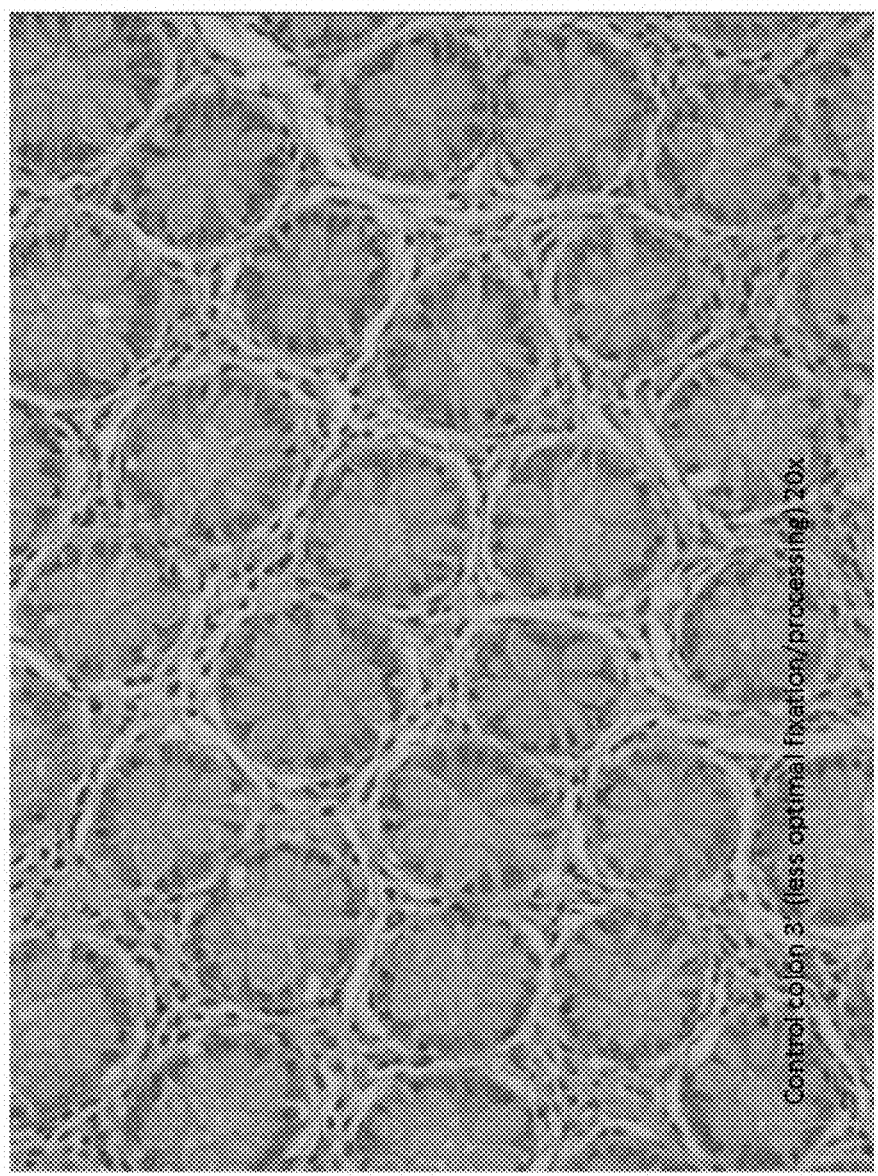
FIG. 20 is the control human colon section of FIG. 19, magnified 20×.
Figure 36:
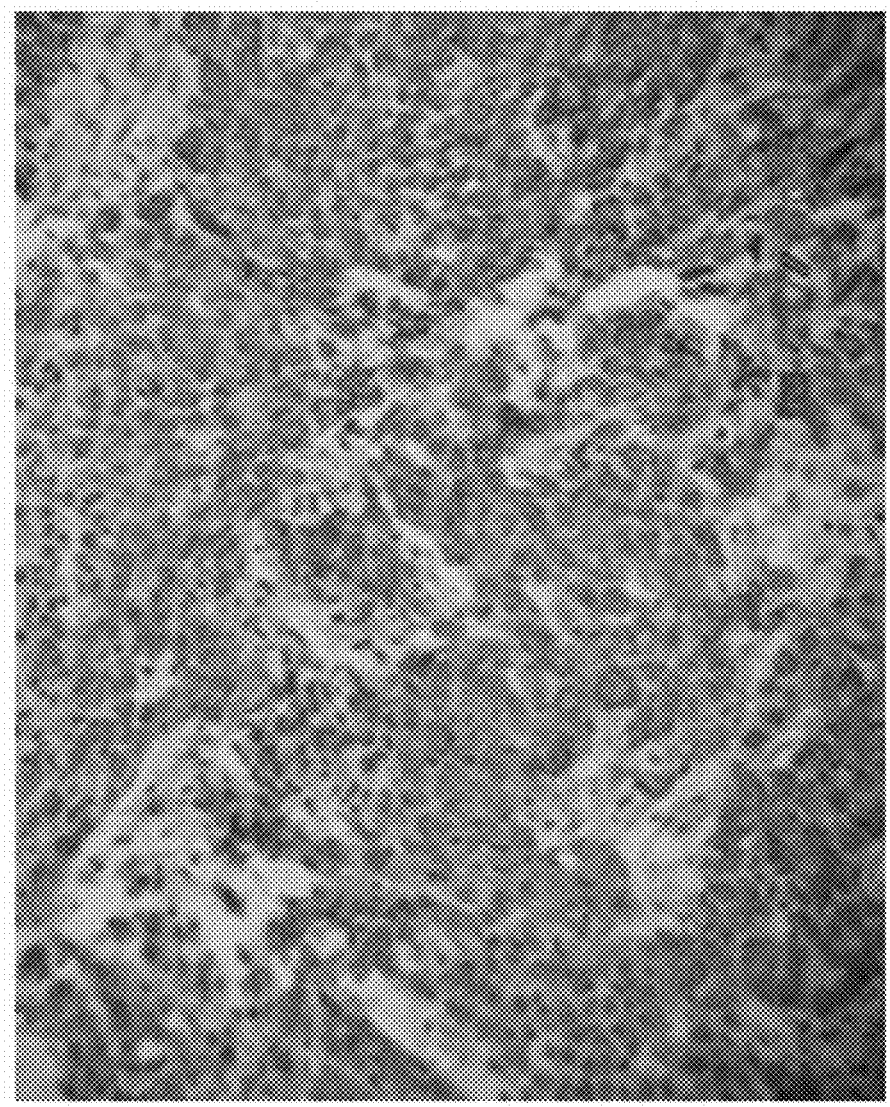
FIG. 36 is a control human colon section prepared according to the method described in Example 3, stained for cytokeratin.

Slides labeled "Control" were prepared using these standard procedures and can be found in FIGS. 1-4, 13-20 and 36.

The methods, compositions, kits and systems described herein sufficiently decrease the time of the process of fixing, dehydrating and clearing of the structure of biological tissue; sufficiently improve the quality of the fixed structure of the biological tissue; prevent any artifacts; maintain the histologic structure on the biologic tissue; and improve the quality of the image of the structure of the biological tissue.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method for fixing a tissue sample comprising:
   (a) contacting the tissue sample with a fixing composition for about 1 minute to about 5 minutes, the fixing composition comprising about 40% v/v DMSO; about 10% v/v of formalin; and a buffering agent;
   (b) dehydrating the tissue sample in a non-aqueous solution comprising DMSO and alcohol;
   (c) clearing the tissue sample in a clearing solution comprising xylene and DMSO;
   (d) infiltrating the tissue sample with paraffin, nitrocellulose, plastic or other suitable embedding agent; and
   (e) embedding the tissue in the embedding agent.

2. The method of claim 1, wherein the dehydration step comprises multiple steps, each successive step comprising contacting the sample with a higher percentage of alcohol.

3. The method of claim 1, wherein the clearing step comprises multiple steps.

4. The method of claim 1, wherein the fixing step is performed for about 1 minute.

5. The method of claim 1, wherein the fixing step is performed for about 2.5 minutes.

6. The method of claim 1, wherein the fixing composition further comprises one or more of water, xylene, xylene substitute, or naphtha.

\* \* \* \* \*